United States Patent
Park et al.

(10) Patent No.: US 10,559,764 B2
(45) Date of Patent: Feb. 11, 2020

(54) FUSED POLYCYCLIC HETEROAROMATIC COMPOUND, ORGANIC THIN FILM INCLUDING COMPOUND AND ELECTRONIC DEVICE INCLUDING ORGANIC THIN FILM

(71) Applicant: Samsung Electronics Co., Ltd., Suwon-si, Gyeonggi-do (KR)

(72) Inventors: Jeong Il Park, Seongnam-si (KR); Eigo Miyazaki, Hwaseong-si (KR); Eun Kyung Lee, Seoul (KR); Ajeong Choi, Suwon-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 0 days.

(21) Appl. No.: 15/008,976

(22) Filed: Jan. 28, 2016

(65) Prior Publication Data
US 2016/0226005 A1    Aug. 4, 2016

(30) Foreign Application Priority Data

Jan. 29, 2015   (KR) .................. 10-2015-0014520
Jan. 21, 2016   (KR) .................. 10-2016-0007798

(51) Int. Cl.
*C07D 517/22*    (2006.01)
*H01L 51/00*     (2006.01)
*C07D 495/22*    (2006.01)
*H01L 51/05*     (2006.01)

(52) U.S. Cl.
CPC ........ *H01L 51/0074* (2013.01); *C07D 495/22* (2013.01); *H01L 51/0541* (2013.01); *H01L 51/0545* (2013.01); *H01L 51/0558* (2013.01)

(58) Field of Classification Search
CPC ............................................... C07D 517/22
See application file for complete search history.

(56) References Cited

U.S. PATENT DOCUMENTS

| | | | |
|---|---|---|---|
| 7,816,673 B2 | 10/2010 | Park et al. | |
| 8,232,546 B2 | 7/2012 | Takimiya et al. | |
| 8,367,717 B2 | 2/2013 | Kastler et al. | |
| 8,816,100 B2 | 8/2014 | Takimiya | |
| 9,954,183 B2 * | 4/2018 | Miyazaki | C07D 517/22 |
| 2008/0142792 A1 | 6/2008 | Park et al. | |
| 2009/0043113 A1 | 2/2009 | Park et al. | |
| 2009/0261300 A1 | 10/2009 | Watanabe | |
| 2010/0065826 A1 | 3/2010 | Takimiya et al. | |
| 2011/0224445 A1 | 9/2011 | Takimiya | |
| 2013/0116447 A1 | 5/2013 | Park et al. | |
| 2013/0163570 A1 | 6/2013 | Zhang et al. | |
| 2013/0277657 A1 | 10/2013 | Park et al. | |
| 2013/0320316 A1 | 12/2013 | Park et al. | |
| 2016/0226005 A1 | 8/2016 | Park et al. | |
| 2016/0372686 A1 | 12/2016 | Hahm et al. | |
| 2017/0098786 A1 | 4/2017 | Kitamura et al. | |
| 2017/0317296 A1 | 11/2017 | Yamamoto et al. | |

FOREIGN PATENT DOCUMENTS

| | | |
|---|---|---|
| CN | 101200471 A | 6/2008 |
| CN | 101528753 A | 9/2009 |
| CN | 103467489 A | 12/2013 |
| EP | 1932847 A1 | 6/2008 |
| EP | 2067782 A1 | 6/2009 |
| EP | 2098527 A1 | 9/2009 |
| EP | 2671880 A1 | 12/2013 |
| EP | 3 050 887 A1 | 8/2016 |
| JP | 2010-150229 | 7/2010 |
| JP | 2010-177643 A | 8/2010 |
| JP | 2010-254599 | 11/2010 |
| JP | 2011-526588 | 10/2011 |
| JP | 4958119 | 6/2012 |
| JP | 2015-170758 | 9/2015 |
| JP | 2017-34247 A | 2/2017 |
| KR | 10-2008-0054553 | 6/2008 |
| KR | 20080100982 A | 11/2008 |
| KR | 20130050266 A | 5/2013 |
| KR | 10-2013-0064776 | 6/2013 |
| KR | 20130118629 A | 10/2013 |
| KR | 20130136938 A | 12/2013 |
| KR | 10-2016-0093550 | 8/2016 |
| WO | WO-2008/050726 A1 | 5/2008 |
| WO | WO-2009/009790 A1 | 1/2009 |
| WO | WO-2016/148170 | 9/2016 |

OTHER PUBLICATIONS

Extended European Search Report dated Jun. 16, 2016 issued in corresponding European Patent Application No. 16152968.0.
Chinese Office Action dated Jan. 29, 2018 issued in corresponding Chinese Application No. 201610064600.3 (English translation provided).
U.S. Appl. No. 16/047,208, filed Jul. 27, 2018.
Extended European Search Report dated Nov. 28, 2018 for EP 18185978.6.
Office Action dated Jun. 20, 2019 issued in co-pending U.S. Appl. No. 16/047,208.
Extended European Search Report dated Apr. 1, 2019, issued in corresponding European Patent Application No. 18185978.6.
Office Action dated Oct. 25, 2019, issued in corresponding U.S. Appl. No. 16/047,208.

* cited by examiner

*Primary Examiner* — Andrew D Kosar
*Assistant Examiner* — John S Kenyon
(74) *Attorney, Agent, or Firm* — Harness, Dickey & Pierce, P.L.C.

(57) ABSTRACT

A fused polycyclic heteroaromatic compound represented by Chemical Formula 1A or 1B that has a compact planar structure in which eight or more rings are fused together.

20 Claims, 1 Drawing Sheet

FUSED POLYCYCLIC HETEROAROMATIC COMPOUND, ORGANIC THIN FILM INCLUDING COMPOUND AND ELECTRONIC DEVICE INCLUDING ORGANIC THIN FILM

CROSS-REFERENCE TO RELATED APPLICATION

This application claims priority to and the benefit of Korean Patent Application Nos. 10-2015-0014520 and 10-2016-0007798 filed in the Korean Intellectual Property Office on Jan. 29, 2015 and Jan. 21, 2016, respectively the entire contents of which are incorporated herein by reference.

BACKGROUND

1. Field

Example embodiments relates to a fused polycyclic heteroaromatic compound, an organic thin film including the same, and an electronic device including the organic thin film.

2. Description of the Related Art

In general, flat display devices, e.g., liquid crystal displays or organic electroluminescent displays, are provided with a variety of thin film transistors (TFTs) to drive them. The TFT may include a gate electrode, source/drain electrodes, and a semiconductor layer that may be activated in response to the operation of the gate electrode. The semiconductor layer may include an organic semiconductor material that is controlled by a current between the source electrode and the drain electrode using an applied gate voltage.

Recently, as an organic semiconductor material for a channel of the thin film transistor, low-molecular-weight organic materials, e.g., pentacene or a polymer organic material (e.g., polythiophene), have been studied. However, the polymer organic materials have relatively low charge mobility and relatively high off-state leakage current. Further, relatively low-molecular-weight organic materials, e.g., pentacene, may have a relatively high charge mobility of about 3.2 to about 5.0 cm2/Vs or more, but may require a relatively expensive apparatus for vacuum deposition at the time of forming a thin film. Therefore, the low-molecular-weight organic material may be unsuitable for use in the preparation of a film having a relatively large area, and processibility may be undesirable.

SUMMARY

Example embodiments provide a relatively low-molecular-weight fused polycyclic heteroaromatic compound that has a compact planar structure in which eight or more aromatic rings are fused together, and thereby exhibits relatively high charge mobility, and furthermore, enables the use of a deposition process or a room-temperature (about 24 to 25° C.) solution process when applied to devices, therefore realizing improved processability.

Example embodiments also provide an organic thin film including the fused polycyclic heteroaromatic compound.

Example embodiments also provide an electronic device including the organic thin film as a carrier transport layer.

According to example embodiments, a fused polycyclic heteroaromatic compound includes one of a compound represented by Chemical Formula 1A, a compound represented by Chemical Formula 1B, and a combination thereof.

[Chemical Formula 1A]

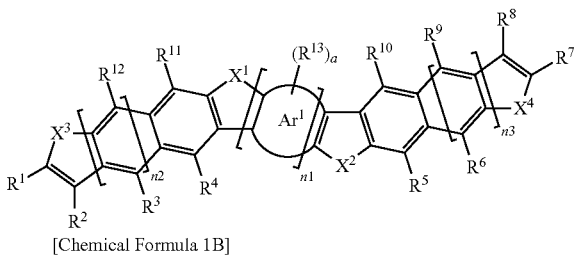

[Chemical Formula 1B]

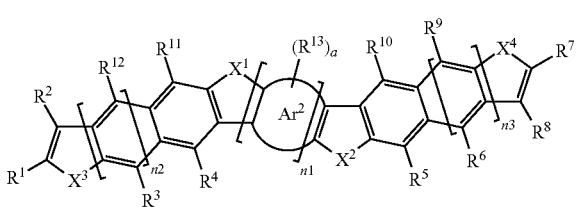

In Chemical Formulae 1A and 1B, each of $Ar^1$ and $Ar^2$ are independently one of phenylene, naphthalene, and anthracene, and a is an integer ranging from 0 to 6, each of $X^1$ to $X^4$ are independently one of O, S, Se, Te, and N—$R^a$, wherein each $R^a$ is independently one of hydrogen, a substituted or unsubstituted linear or branched $C_1$ to $C_{30}$ alkyl group, a substituted or unsubstituted $C_2$ to $C_{30}$ alkenyl group, a substituted or unsubstituted $C_2$ to $C_{30}$ alkynyl group, a substituted or unsubstituted $C_7$ to $C_{30}$ arylalkyl group, a substituted or unsubstituted $C_6$ to $C_{30}$ aryl group, a substituted or unsubstituted $C_1$ to $C_{30}$ alkoxy group, —$OR^b$, wherein $R^b$ is a substituted or unsubstituted $C_6$ to $C_{30}$ aryl group, a substituted or unsubstituted $C_4$ to $C_{30}$ cycloalkyl group, —$OR^c$, wherein $R^c$ is a substituted or unsubstituted $C_4$ to $C_{30}$ cycloalkyl group, a substituted or unsubstituted $C_2$ to $C_{30}$ heteroaryl group, —C(=O)$R^d$, wherein $R^d$ is a substituted or unsubstituted $C_1$ to $C_{30}$ alkyl group, —S(=O)$_2R^e$, wherein $R^e$ is a substituted or unsubstituted $C_1$ to $C_{30}$ alkyl group, and —NHC(=O)$OR^f$, wherein $R^f$ is a substituted or unsubstituted $C_1$ to $C_{30}$ alkyl group, each of $R^1$ to $R^{13}$ are independently one of hydrogen, a substituted or unsubstituted $C_1$ to $C_{30}$ alkyl group, a substituted or unsubstituted $C_1$ to $C_{30}$ alkoxy group, a substituted or unsubstituted $C_2$ to $C_{30}$ alkenyl group, a substituted or unsubstituted $C_2$ to $C_{30}$ alkynyl group, a substituted or unsubstituted $C_6$ to $C_{30}$ aryl group, a substituted or unsubstituted $C_2$ to $C_{30}$ heteroaryl group, a substituted or unsubstituted $C_7$ to $C_{30}$ arylalkyl group, a substituted or unsubstituted $C_2$ to $C_{30}$ heteroarylalkyl group, a substituted or unsubstituted $C_2$ to $C_{30}$ alkylheteroaryl group, a substituted or unsubstituted $C_5$ to $C_{30}$ cycloalkyl group, and a substituted or unsubstituted $C_2$ to $C_{30}$ heterocycloalkyl group, n1 is 0 or 1, each of n2 and n3 are independently 0, 1, 2, or 3, when n1 is 0, n2 and n3 are an integer of 1, 2, or 3, and when n1 is 1, n1+n2+n3≥2, for example, neither of n2 and n3 are 0.

Each of the $R^1$ and $R^7$ may independently be one of a substituted or unsubstituted $C_1$ to $C_{30}$ alkyl group, a substituted or unsubstituted $C_6$ to $C_{30}$ aryl group, a substituted or unsubstituted $C_2$ to $C_{30}$ heteroaryl group, a substituted or unsubstituted $C_7$ to $C_{30}$ arylalkyl group, a substituted or unsubstituted $C_2$ to $C_{30}$ heteroarylalkyl group, a substituted or unsubstituted $C_2$ to $C_{30}$ alkylheteroaryl group, a substituted or unsubstituted $C_5$ to $C_{30}$ cycloalkyl group, and a substituted or unsubstituted $C_2$ to $C_{30}$ heterocycloalkyl group.

Each of the $R^1$ and $R^7$ may independently be a fluoro-substituted $C_1$ to $C_{30}$ alkyl group.

The $R^a$ may be, for example, one of a substituted or unsubstituted $C_{10}$ to $C_{30}$ alkyl group, a substituted or unsubstituted $C_{10}$ to $C_{30}$ alkoxy group, a substituted or unsubstituted $C_{10}$ to $C_{30}$ alkenyl group, and a substituted or unsubstituted $C_{10}$ to $C_{30}$ alkynyl group, for another example, a fluoro-substituted $C_1$ to $C_{30}$ alkyl group, for a further example, a $C_1$ to $C_{30}$ perfluoro alkyl group ($C_nF_{2n+1}$, wherein n is an integer of 1 or more) or a fluoro-substituted $C_{10}$ to $C_{30}$ alkyl group, and for a further example, a $C_{10}$ to $C_{30}$ perfluoro alkyl group ($C_nF_{2n+1}$, wherein n is an integer of 10 to 30).

The fused polycyclic heteroaromatic compound may have a molecular weight of about 350 to about 3,000.

According to example embodiments, an organic thin film includes the fused polycyclic heteroaromatic compound.

According to example embodiments, an electronic device includes the fused polycyclic heteroaromatic compound.

The electronic device may be one of a transistor, an organic light emitting diode (OLED), a photovoltaic device, a solar cell, a laser device, a memory device, and a sensor.

The electronic device may include at least one charge transport layer, and the charge transport layer may include the fused polycyclic heteroaromatic compound.

According to example embodiments, a compound includes a compact planar structure including at least eight rings fused to each other, the compound represented by one of Chemical Formula 1A, Chemical Formula 1B, and a combination thereof:

[Chemical Formula 1A]

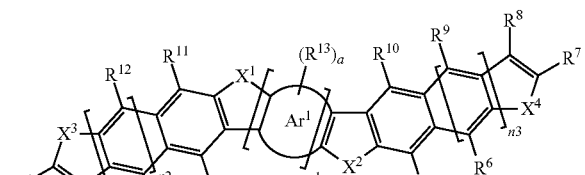

[Chemical Formula 1B]

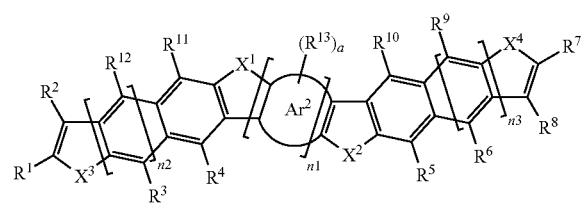

wherein, in Chemical Formulae 1A and 1B, each of $Ar^1$ and $Ar^2$ are independently one of phenylene and naphthalene, and a is an integer ranging from 0 to 6, each of $X^1$ to $X^4$ are independently one of S, Se, and N—$R^a$, wherein each $R^a$ are independently one of hydrogen, a substituted or unsubstituted linear or branched $C_1$ to $C_{30}$ alkyl group, a substituted or unsubstituted $C_2$ to $C_{30}$ alkenyl group, a substituted or unsubstituted $C_2$ to $C_{30}$ alkynyl group, a substituted or unsubstituted $C_7$ to $C_{30}$ arylalkyl group, a substituted or unsubstituted $C_6$ to $C_{30}$ aryl group, a substituted or unsubstituted $C_1$ to $C_{30}$ alkoxy group, —$OR^b$, wherein $R^b$ is a substituted or unsubstituted $C_6$ to $C_{30}$ aryl group, a substituted or unsubstituted $C_4$ to $C_{30}$ cycloalkyl group, —$OR^c$, wherein $R^c$ is a substituted or unsubstituted $C_4$ to $C_{30}$ cycloalkyl group, a substituted or unsubstituted $C_2$ to $C_{30}$ heteroaryl group, —C(=O)$R^d$, wherein $R^d$ is a substituted or unsubstituted $C_1$ to $C_{30}$ alkyl group, —S(=O)$_2$ $R^e$, wherein $R^e$ is a substituted or unsubstituted $C_1$ to $C_{30}$ alkyl group, and —NHC(=O)$OR^f$, wherein $R^f$ is a substituted or unsubstituted $C_1$ to $C_{30}$ alkyl group, each of $R^1$ to $R^{13}$ are independently one of hydrogen, a substituted or unsubstituted $C_1$ to $C_{30}$ alkyl group, and a substituted or unsubstituted $C_6$ to $C_{30}$ aryl group, n1 is 0 or 1, and each of n2 and n3 are independently 0, 1, 2, or 3.

DETAILED DESCRIPTION

Figure 1:
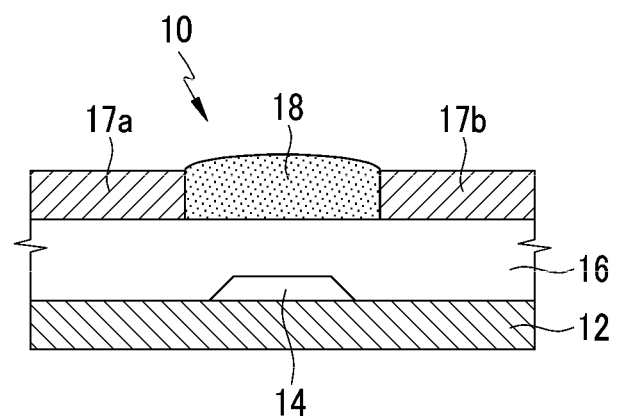
FIG. 1 is a schematic cross-sectional view showing a transistor according to example embodiments.

The present disclosure will be described more fully hereinafter with reference to the accompanying drawings, in which example embodiments of this disclosure are shown. However, this disclosure may be embodied in many different forms, and is not to be construed as limited to the example embodiments set forth herein.

In the drawings, the thickness of layers, films, panels, regions, etc., are exaggerated for clarity.

It will be understood that when an element such as a layer, film, region, or substrate is referred to as being "on" another element, it may be directly on the other element or intervening elements may also be present. In contrast, when an element is referred to as being "directly on" another element, there are no intervening elements present.

Example embodiments of the present inventive concepts will hereinafter be described in detail, and may be more easily performed by those who have common knowledge in the related art. However, this disclosure may be embodied in many different forms and is not construed as limited to the example embodiments set forth herein.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

In the drawings, parts having no relationship with the description are omitted for clarity of the embodiments, and the same or similar constituent elements are indicated by the same reference numerals throughout the specification.

It will be understood that when an element is referred to as being "on," "connected" or "coupled" to another element, it can be directly on, connected or coupled to the other element or intervening elements may be present. In contrast, when an element is referred to as being "directly on," "directly connected" or "directly coupled" to another element, there are no intervening elements present. As used herein the term "and/or" includes any and all combinations of one or more of the associated listed items. Further, it will be understood that when a layer is referred to as being "under" another layer, it can be directly under or one or more intervening layers may also be present. In addition, it will also be understood that when a layer is referred to as being "between" two layers, it can be the only layer between the two layers, or one or more intervening layers may also be present.

It will be understood that, although the terms "first", "second", etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of example embodiments.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein. As used herein, expressions such as "at least one of," when preceding a list of elements, modify the entire list of elements and do not modify the individual elements of the list.

As used herein, the term "combination thereof" refers to a mixture, a stacked structure, etc.

As used herein, when a definition is not otherwise provided, the prefix "hetero" may refer to a group that includes at least one ring member (e.g., 1 to 4 ring members) that is a heteroatom (e.g., 1 to 4 heteroatoms, each independently one of N, O, S, Si, and P). The total number of ring members may be 3 to 10. If multiple rings are present, each ring is independently aromatic, saturated, or partially unsaturated, and multiple rings, if present, may be fused, pendant, spirocyclic, or a combination thereof. Heterocycloalkyl groups include at least one non-aromatic ring that contains a heteroatom ring member. Heteroaryl groups include at least one aromatic ring that contains a heteroatom ring member. Non-aromatic and/or carbocyclic rings may also be present in a heteroaryl group, provided that at least one ring is both aromatic and contains a ring member that is a heteroatom.

As used herein, when a definition is not otherwise provided, the term "alkyl group" may be a linear or branched saturated monovalent hydrocarbon group (e.g., a methyl group, an ethyl group, a propyl group, an isobutyl group, a sec-butyl group, a tert-butyl group, a pentyl group, an iso-amyl group, a hexyl group, etc).

The term "alkenyl group" may refer to a linear or branched monovalent hydrocarbon group including at least one carbon-carbon double bond (e.g., an ethenyl group).

The term "alkynyl group" may refer to a linear or branched monovalent hydrocarbon group including at least one carbon-carbon triple bond (e.g., ethynyl group).

The term "alkoxy group" may refer to an alkyl group that is linked via an oxygen atom, e.g., a methoxy, an ethoxy, and a sec-butyloxy group.

The term "aryl group" may refer to a monovalent functional group formed by the removal of one hydrogen atom from a ring of an arene, e.g., phenyl or naphthyl. The arene may refer to a hydrocarbon having an aromatic ring, and includes monocyclic and polycyclic hydrocarbons, wherein the additional ring(s) of the polycyclic hydrocarbon may be aromatic or nonaromatic.

The term "aryloxy group" may refer to an aryl group that is linked via an oxygen atom, and the aryl group is the same as described above.

The "arylalkyl group" may refer to an aryl group where at least one hydrogen atom is substituted with a lower alkylene, e.g., methylene, ethylene, propylene, etc. For example, the "arylalkyl group" may be a benzyl group or a phenylethyl group.

The term "cycloalkyl group" may refer to a monovalent functional group having one or more saturated rings in which all ring members are carbon, e.g., a cyclopentyl group and a cyclohexyl group.

The term "heteroarylalkyl group" may refer to the alkyl group defined above where at least one hydrogen atom is substituted with a heteroaryl group.

The term "alkylheteroaryl group" may refer to the heteroaryl group defined above, where at least one hydrogen atom is substituted with an alkyl group.

As used herein, when a definition is not otherwise provided, the term "aromatic ring" refers to a functional group in which all atoms in the cyclic functional group have a p-orbital, and wherein these p-orbitals are conjugated. For example, the aromatic ring may be a $C_6$ to $C_{20}$ aryl group.

As used herein, when a definition is not otherwise provided, the term "substituted" means that a compound or group is substituted with at least one substituent independently selected from a halogen (—F, —Cl, —Br, or —I), a $C_1$ to $C_{30}$ linear or branched alkyl group, for example, a $C_1$ to $C_{10}$ linear or branched alkyl group, a $C_2$ to $C_{30}$ linear or branched alkenyl group, for example, a $C_2$ to $C_{10}$ linear or branched alkenyl group, a $C_2$ to $C_{30}$ linear or branched alkynyl group, for example, a $C_2$ to $C_{10}$ linear or branched alkynyl group, a $C_6$ to $C_{30}$ aryl group, for example, a $C_6$ to $C_{12}$ aryl group, a $C_2$ to $C_{30}$ heteroaryl group, for example, a $C_2$ to $C_{12}$ heteroaryl group, a $C_3$ to $C_{30}$ cycloalkyl group, a $C_1$ to $C_{20}$ fluoroalkyl group, a $C_1$ to $C_{20}$ perfluoroalkyl group (CnF2n+1), a $C_1$ to $C_{30}$ linear or branched alkoxy group, a $C_3$ to $C_{30}$ cycloalkoxy group, a $C_2$ to $C_{30}$ linear or branched alkoxyalkyl group, a $C_4$ to $C_{30}$ cycloalkoxyalkyl group, a cyano group, an amino group (—NRR', wherein R and R' are independently hydrogen or a $C_1$ to $C_{10}$ alkyl group), an amidino group (—C(=NH)NH$_2$), a nitro group (—NO$_2$), an amide group (—C(=O)N(H)R, wherein R is hydrogen or a $C_1$ to $C_{10}$ alkyl group), an aldehyde group (—C(=O)H), a hydroxy group (—OH), a sulfonyl group (—S(=O)$_2$R, wherein R is hydrogen or a $C_1$ to $C_{10}$ alkyl group), and a carbamate group (—NHC(=O)OR, wherein R is a $C_1$ to $C_{10}$ alkyl group), instead of hydrogen of a functional group or a compound, provided that the substituted atom's normal valence is not exceeded.

According to example embodiments, a fused polycyclic heteroaromatic compound has a compact planar structure in which eight or more aromatic rings may be fused together and represented by one of Chemical Formula 1A and 1B.

[Chemical Formula 1A]

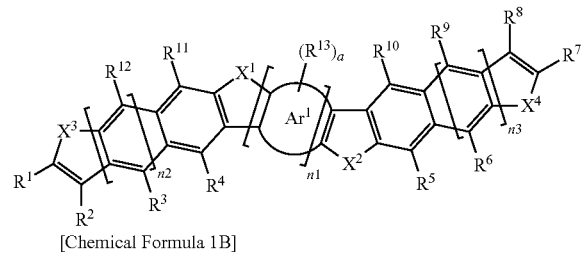

[Chemical Formula 1B]

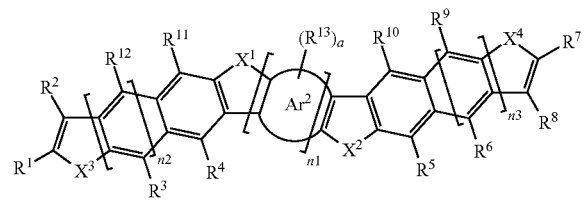

In Chemical Formulae 1A and 1B, each of $Ar^1$ and $Ar^2$ are independently one of phenylene, naphthalene, and anthracene, and a is an integer ranging from 0 to 6, each of $X^1$ to $X^4$ are independently one of O, S, Se, Te, and N—$R^a$, wherein each $R^a$ is independently one of hydrogen, a substituted or unsubstituted linear or branched $C_1$ to $C_{30}$ alkyl group, a substituted or unsubstituted $C_2$ to $C_{30}$ alkenyl group, a substituted or unsubstituted $C_2$ to $C_{30}$ alkynyl group, a substituted or unsubstituted $C_7$ to $C_{30}$ arylalkyl group, a substituted or unsubstituted $C_6$ to $C_{30}$ aryl group, a substituted or unsubstituted $C_1$ to $C_{30}$ alkoxy group, —$OR^b$, wherein $R^b$ is a substituted or unsubstituted $C_6$ to $C_{30}$ aryl group, a substituted or unsubstituted $C_4$ to $C_{30}$ cycloalkyl group, —$OR^c$, wherein $R^c$ is a substituted or unsubstituted $C_4$ to $C_{30}$ cycloalkyl group, a substituted or unsubstituted $C_2$ to $C_{30}$ heteroaryl group, —C(=O)$R^d$, wherein $R^d$ is a substituted or unsubstituted $C_1$ to $C_{30}$ alkyl group, —S(=O)$_2R^e$, wherein $R^e$ is a substituted or unsubstituted $C_1$ to $C_{30}$ alkyl group, and —NHC(=O)O$R^f$, wherein $R^f$ is a substituted or unsubstituted $C_1$ to $C_{30}$ alkyl group, each $R^1$ to $R^{13}$ are independently one of hydrogen, a substituted or unsubstituted $C_1$ to $C_{30}$ alkyl group, a substituted or unsubstituted $C_1$ to $C_{30}$ alkoxy group, a substituted or unsubstituted $C_2$ to $C_{30}$ alkenyl group, a substituted or unsubstituted $C_2$ to $C_{30}$ alkynyl group, a substituted or unsubstituted $C_6$ to $C_{30}$ aryl group, a substituted or unsubstituted $C_2$ to $C_{30}$ heteroaryl group, a substituted or unsubstituted $C_7$ to $C_{30}$ arylalkyl group, a substituted or unsubstituted $C_2$ to $C_{30}$ heteroarylalkyl group, a substituted or unsubstituted $C_2$ to $C_{30}$ alkylheteroaryl group, a substituted or unsubstituted $C_5$ to $C_{30}$ cycloalkyl group, and a substituted or unsubstituted $C_2$ to $C_{30}$ heterocycloalkyl group, n1 is 0 or 1, each of n2 and n3 are independently 0, 1, 2, or 3, when n1 is 0, n2 and n3 are an integer of 1, 2, or 3, and when n1 is 1, n1+n2+n3≥2.

In Chemical Formulae 1A and 1B, when $Ar^1$ and $Ar^2$ are phenylene, a is an integer of 0 to 2, when $Ar^1$ and $Ar^2$ are naphthalene, a is an integer of 0 to 4, and when $Ar^1$ and $Ar^2$ are anthracene, a is an integer of 0 to 6.

The $R^1$ and $R^7$ may be one of a substituted or unsubstituted $C_1$ to $C_{30}$ alkyl group, for example a substituted or unsubstituted $C_8$ to $C_{30}$ alkyl group, a substituted or unsubstituted $C_6$ to $C_{30}$ aryl group and a substituted or unsubstituted $C_2$ to $C_{30}$ heteroaryl group, a substituted or unsubstituted $C_7$ to $C_{30}$ arylalkyl group, a substituted or unsubstituted $C_2$ to $C_{30}$ heteroarylalkyl group, a substituted or unsubstituted $C_2$ to $C_{30}$ alkylheteroaryl group, a substituted or unsubstituted $C_5$ to $C_{30}$ cycloalkyl group, and a substituted or unsubstituted $C_2$ to $C_{30}$ heterocycloalkyl group.

The $R^1$ and $R^7$ may be a fluoro-substituted $C_1$ to $C_{30}$ alkyl group.

Examples of the $R^a$ may be one of a substituted or unsubstituted $C_{10}$ to $C_{30}$ alkyl group, a substituted or unsubstituted $C_{10}$ to $C_{30}$ alkoxy group, a substituted or unsubstituted $C_{10}$ to $C_{30}$ alkenyl group, or a substituted or unsubstituted $C_{10}$ to $C_{30}$ alkynyl group, and other examples of the Ra may be a fluoro-substituted $C_1$ to $C_{30}$ alkyl group, for example, a $C_1$ to $C_{30}$ perfluoro alkyl group ($C_nF_{2n+1}$, wherein n is an integer of 1 or more) and a fluoro-substituted $C_{10}$ to $C_{30}$ alkyl group, for example, a $C_{10}$ to $C_{30}$ perfluoro alkyl group ($C_nF_{2n+1}$, wherein n is an integer of 10 to 30).

The fused polycyclic heteroaromatic compound represented by the Chemical Formula 1A or 1B has a structure in which eight or more aromatic rings and hetero aromatic rings are fused together. In Chemical Formulae 1A and 1B, when n1 is 0, each of n2 and n3 are independently 1, 2, or 3, when n1 is 1, n1+n2+n3≥2, for example, neither of n2 and n3 are 0. By having a compact planar molecular structure, the fused polycyclic heteroaromatic compound has a relatively uniform and stable oxidation potential when applied to an actual device, and exhibits relatively high charge mobility because the intermolecular packing and stacking are improved. Thereby, the fused polycyclic heteroaromatic compound is more easily synthesized to be effectively applied to a semiconductor material, an electron transporting material, etc.

In Chemical Formula 1A or 1B, $X^1$, $X^2$, $X^3$, and $X^4$ are present so that the same elements are positioned to be symmetrical to each other, improving packing or stacking characteristics.

In Chemical Formula 1A or 1B, by positioning at least one fused benzene ring among hetero cycles, a conjugation structure is expanded, and thus interaction among molecules is increased, resulting in improved charge mobility and thermal stability.

In addition, by positioning a hetero-ring between benzene rings, the solubility of the fused polycyclic heteroaromatic compound in an organic solvent may be improved. By introducing a $C_{10}$ to $C_{30}$ long aliphatic chain group (e.g., a substituted or unsubstituted $C_{10}$ to $C_{30}$ alkyl group or a substituted or unsubstituted $C_{10}$ to $C_{30}$ alkenyl group) into $R^1$ to $R^{13}$ of the Chemical Formula 1A and 1B, solubility of the fused polycyclic heteroaromatic compound may be improved. Due to the solubility improvement, the fused polycyclic heteroaromatic compound may be simply coated by a solution process at room temperature as well as in a deposition process, and the thin film may be formed in a relatively wide area so the processibility and the workability are improved.

When $X^1$ to $X^4$ are N—$R^a$, examples of the $R^a$ may be one of a substituted or unsubstituted $C_{10}$ to $C_{30}$ alkyl group, a substituted or unsubstituted $C_{10}$ to $C_{30}$ alkoxy group, a substituted or unsubstituted $C_{10}$ to $C_{30}$ alkenyl group, and a substituted or unsubstituted $C_{10}$ to $C_{30}$ alkynyl group, for another example, a fluoro-substituted $C_1$ to $C_{30}$ alkyl group, for example, a $C_1$ to $C_{30}$ perfluoro alkyl group ($C_nF_{2n+1}$, wherein n is an integer of 1 or more) or a fluoro-substituted $C_{10}$ to $C_{30}$ alkyl group, or for example, a $C_{10}$ to $C_{30}$ perfluoro alkyl group ($C_nF_{2n+1}$, wherein n is an integer of 10 to 30). The introduction of these substituents may increase interaction among molecules and advantageously arrange the molecules, and thus improve charge mobility. In addition, the introduction of the substituents may improve solubility of the fused polycyclic heteroaromatic compound, and thus facilitate synthesis of the compound and promote its mass production, and a solution process may also be easily performed during formation of a thin film.

The fused polycyclic heteroaromatic compound according to example embodiments has a hetero aromatic ring as the outermost ring and thus may have a desirable structure for a molecular arrangement. Because the hetero aromatic ring increases an interaction among molecules, charge mobility may be improved.

The fused polycyclic heteroaromatic compound according to example embodiments may have a molecular weight of about 300 to about 3,000. Within the range of the molecular weight, the fused polycyclic heteroaromatic compound may be relatively easy to handle.

Examples of the fused polycyclic heteroaromatic compound may include the following compounds (1) to (58).

[Compounds (1) to (58)]

(1)
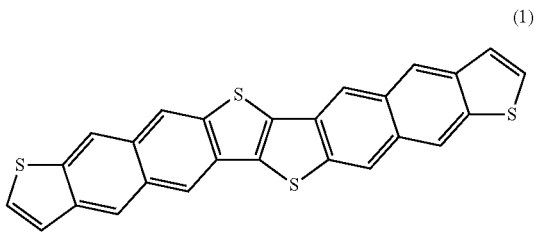

(2)
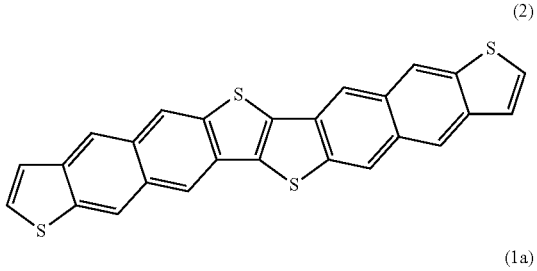

(1a)
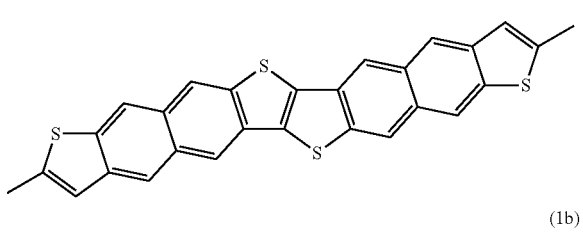

(1b)
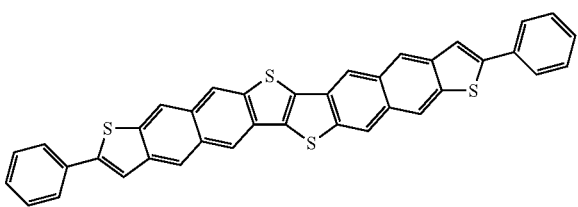

(3)
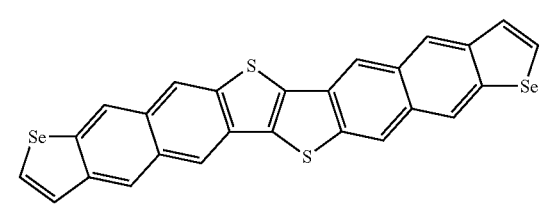

(4)
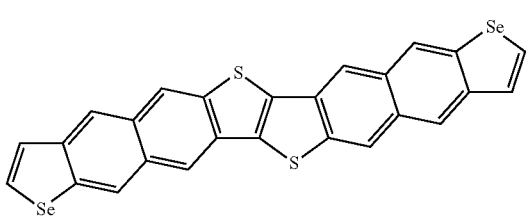

(5)
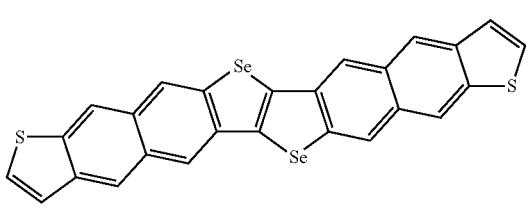

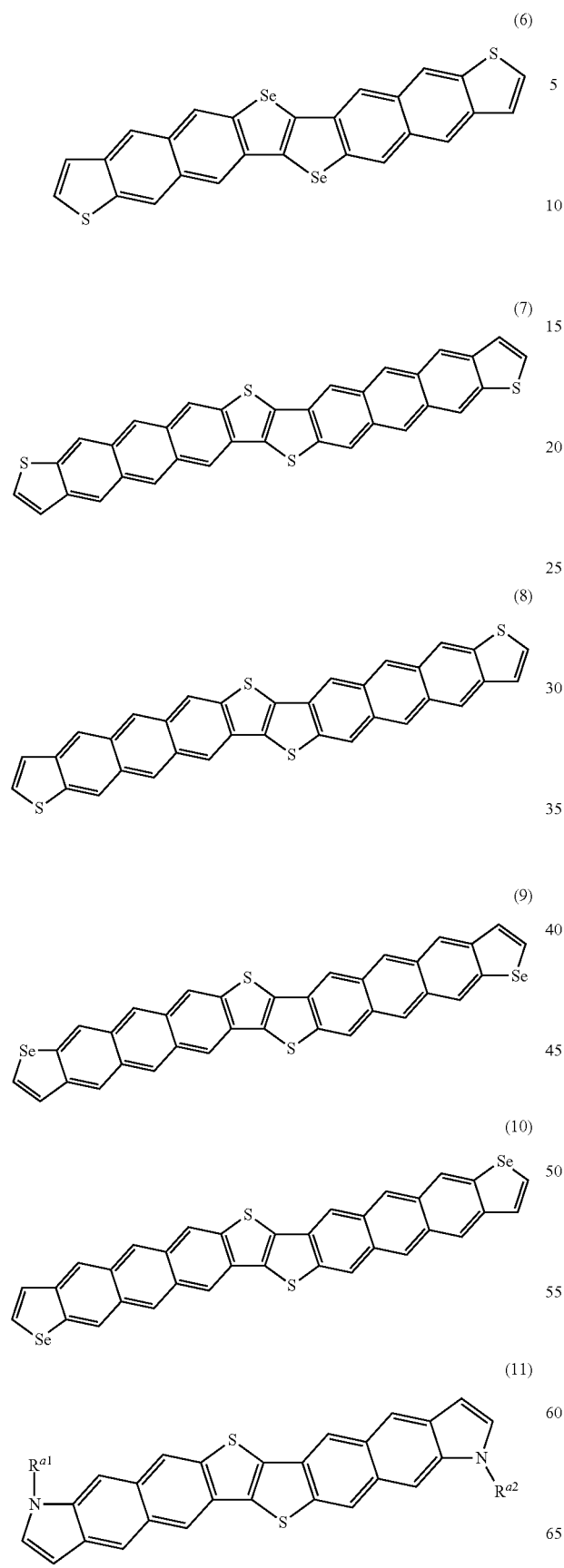
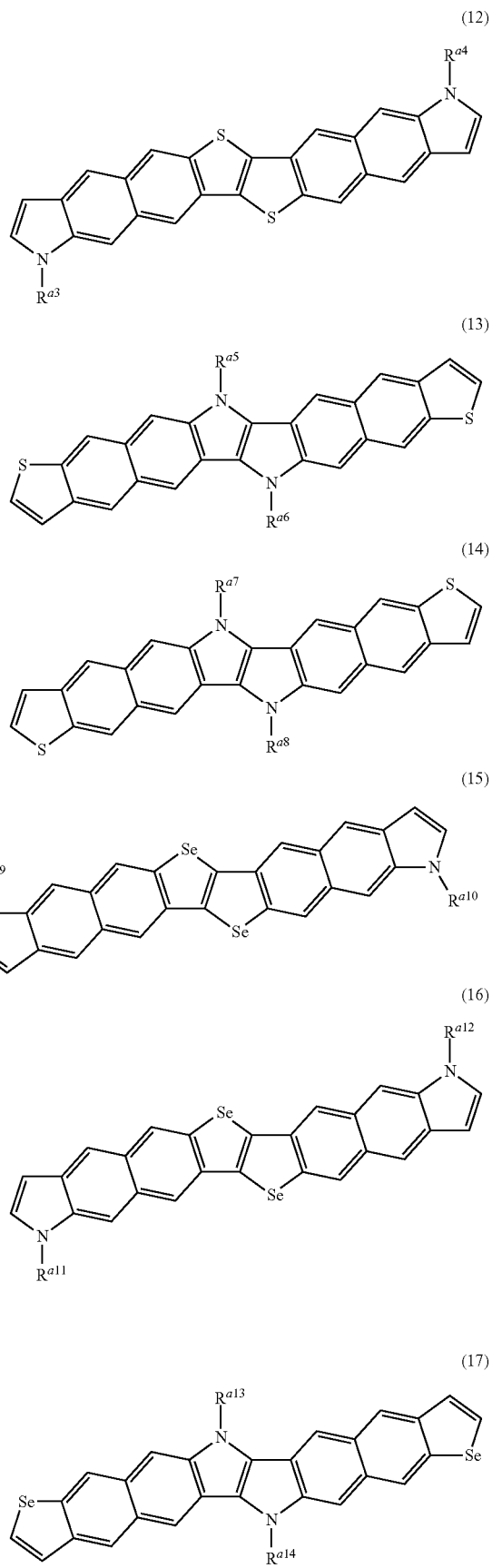

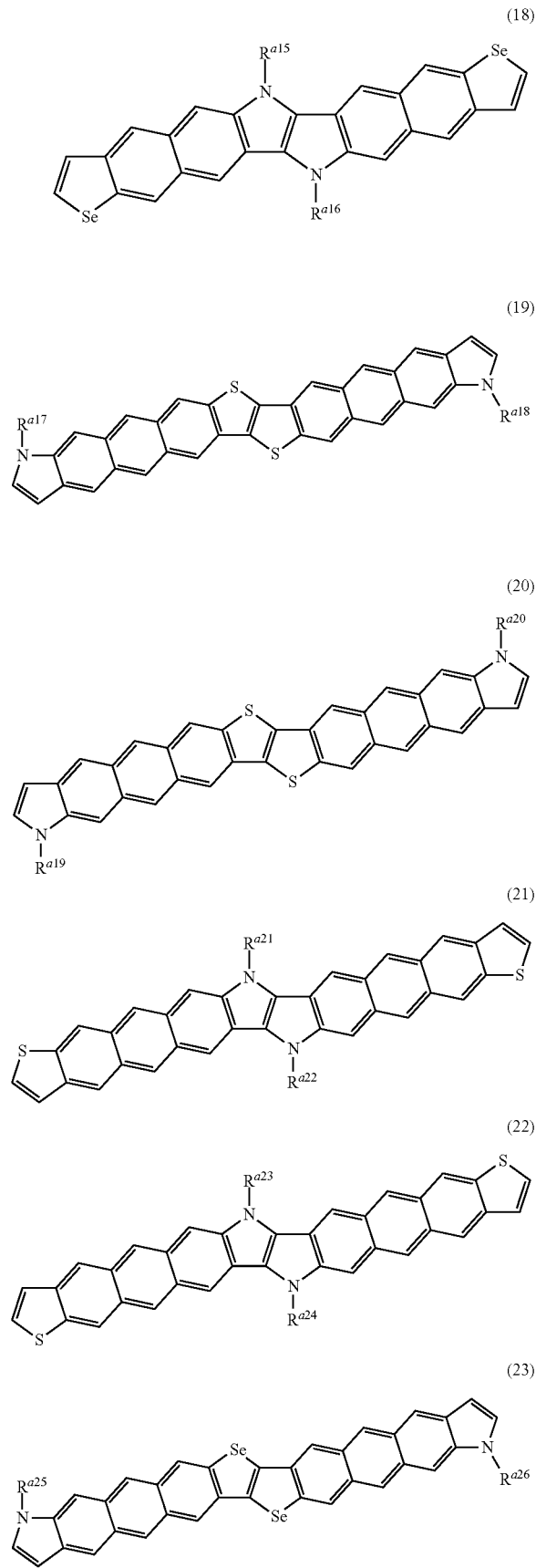
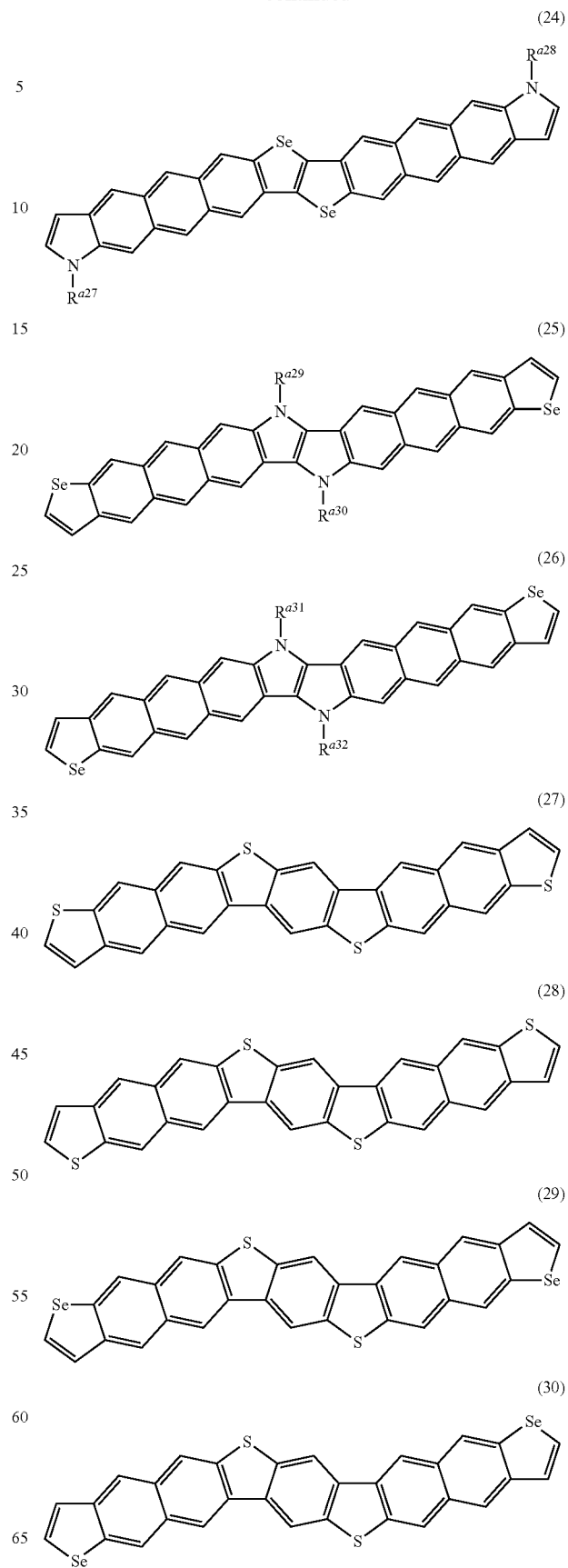

(31)
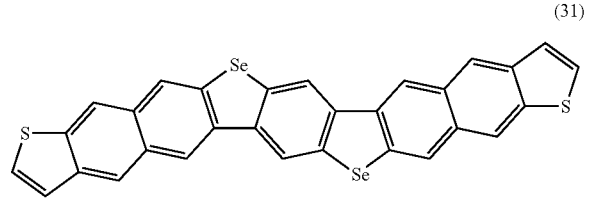
(32)
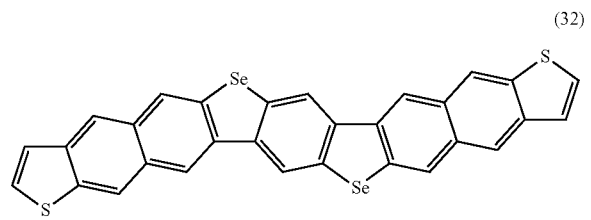
(33)
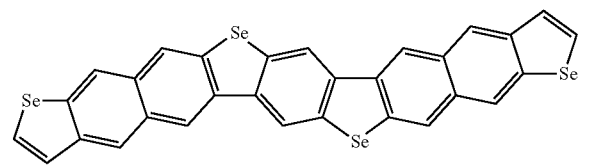
(34)
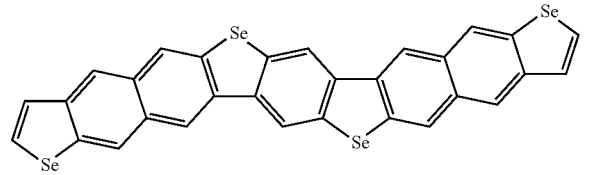
(35)
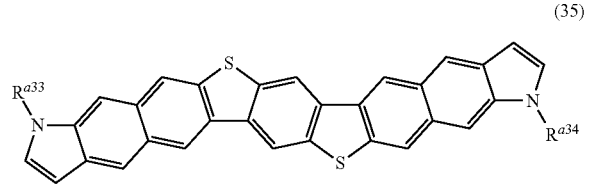
(36)
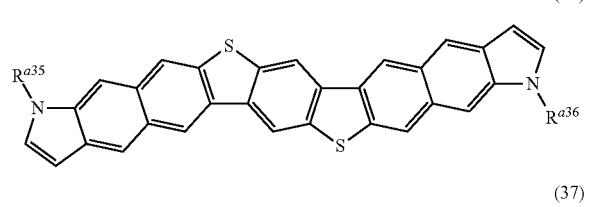
(37)
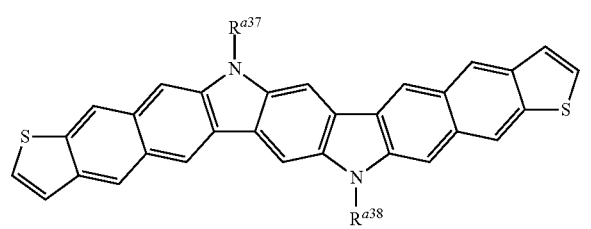
(38)
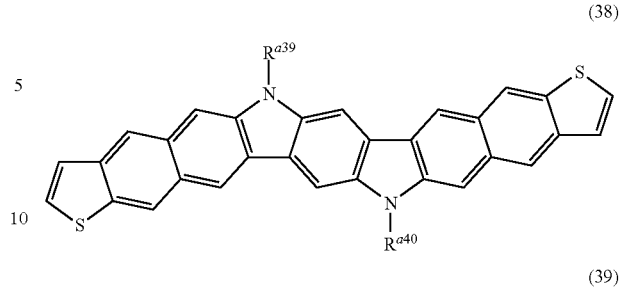
(39)
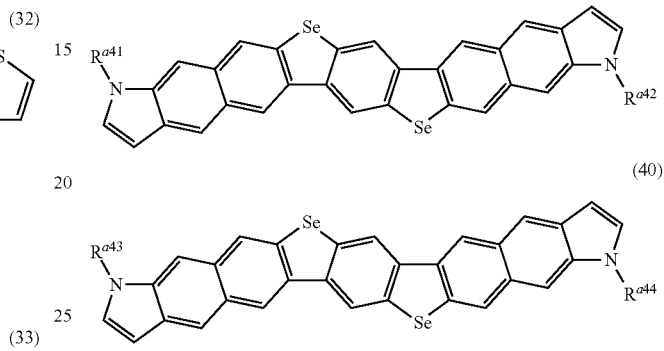
(40)
(41)
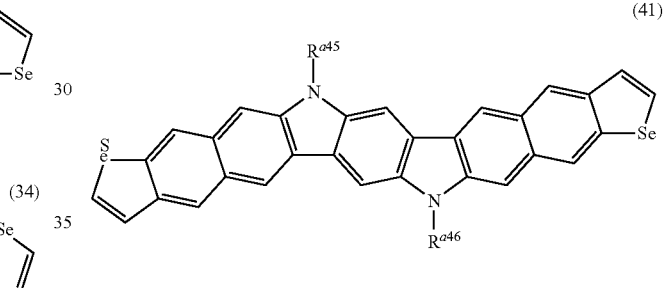
(42)
(43)
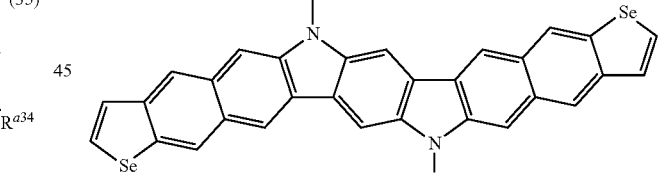
(44)
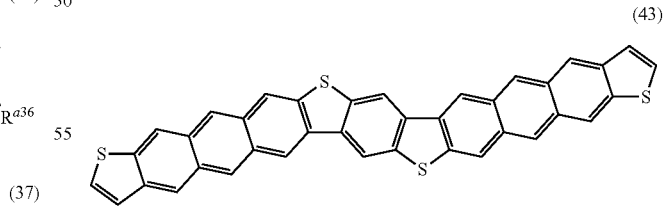
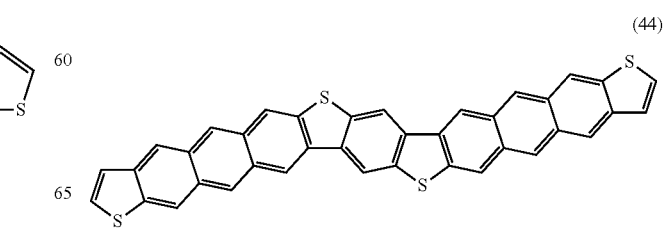

(45)
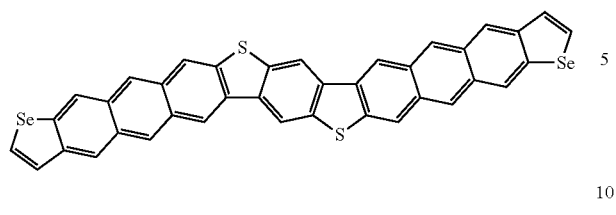
(46)
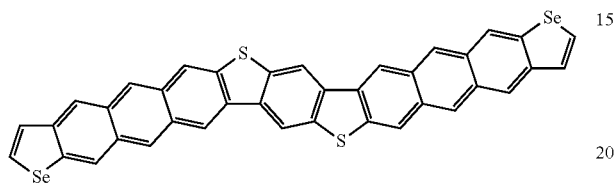
(47)
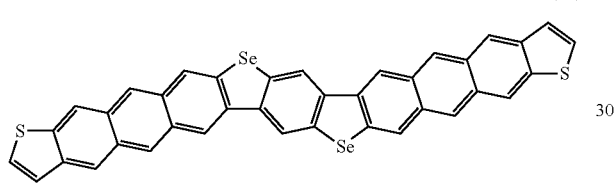
(48)
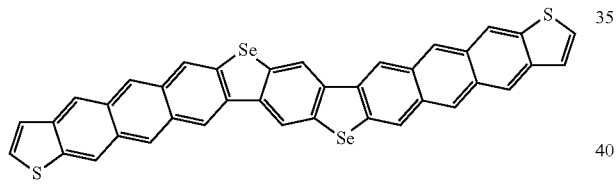
(49)
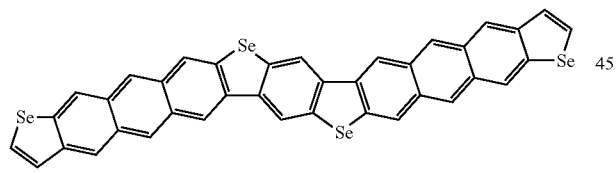
(50)
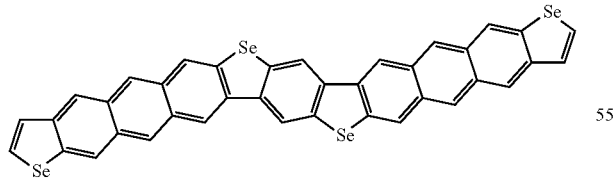
(51)
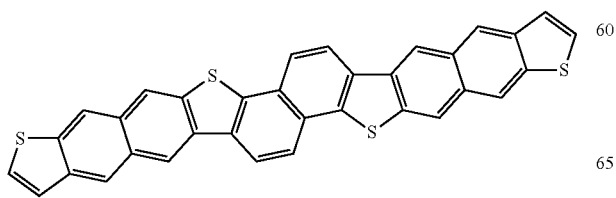
(52)
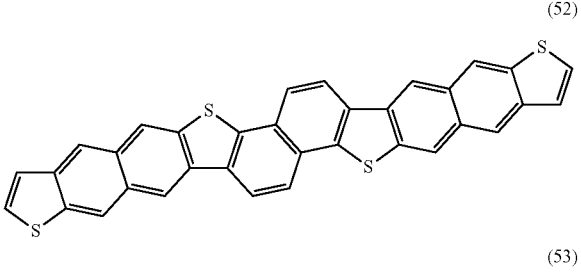
(53)
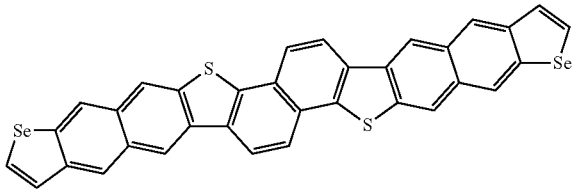
(54)
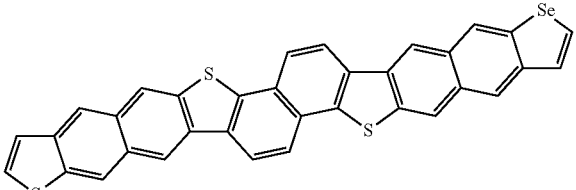
(55)
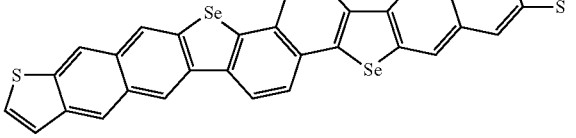
(56)
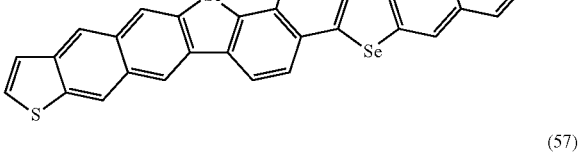
(57)
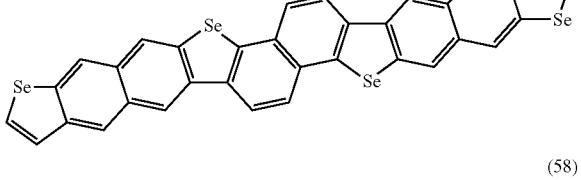
(58)
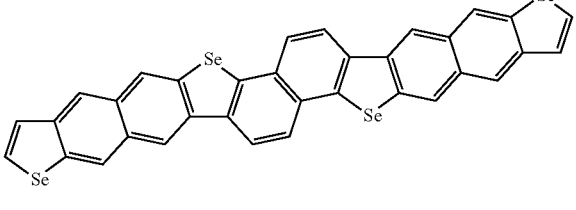

In the compounds (1) to (58), the hydrogen of each benzene ring, each thiophene ring, each selenophene ring or each pyrrole ring may be replaced by a substituted or unsubstituted $C_1$ to $C_{30}$ alkyl group, a substituted or unsubmobility according to Marcus theory. For comparison, the HOMO energy, reorganization energy, and expectation mobility of compounds of Ref-1, Ref-2 and Ref-3a are also shown in Table 1.

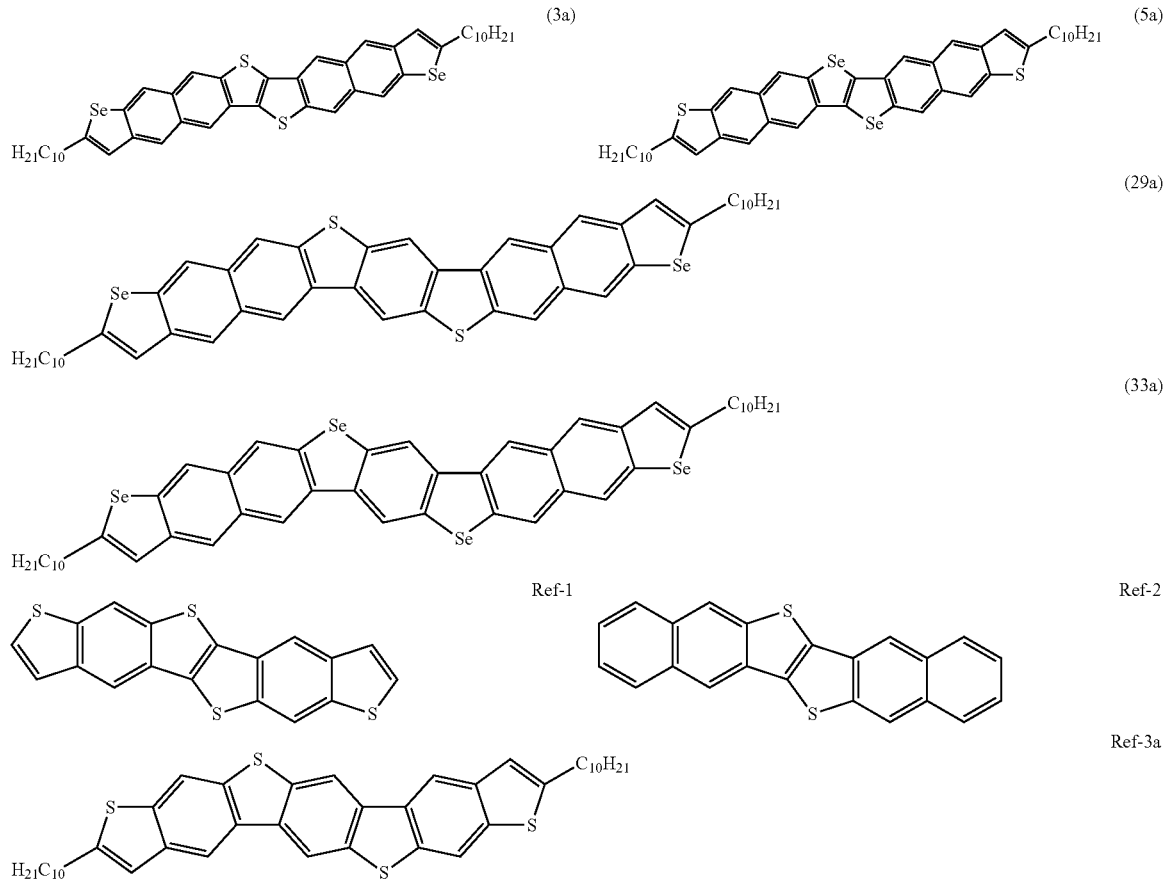

stituted $C_1$ to $C_{30}$ alkoxy group, a substituted or unsubstituted $C_2$ to $C_{30}$ alkenyl group, a substituted or unsubstituted $C_2$ to $C_{30}$ alkynyl group, a substituted or unsubstituted $C_6$ to $C_{30}$ aryl group, a substituted or unsubstituted $C_2$ to $C_{30}$ heteroaryl group, a substituted or unsubstituted $C_7$ to $C_{30}$ arylalkyl group, a substituted or unsubstituted $C_2$ to $C_{30}$ heteroarylalkyl group, a substituted or unsubstituted $C_2$ to $C_{30}$ alkylheteroaryl group, a substituted or unsubstituted $C_5$ to $C_{30}$ cycloalkyl group, or a substituted or unsubstituted $C_2$ to $C_{30}$ heterocycloalkyl group.

$R^{a1}$ to $R^{a48}$ of the compounds (11) to (26) and (35) to (42) are independently the same as $R^a$ of Chemical Formulae 1A and 1B, and may be, for example, one of hydrogen, a substituted or unsubstituted linear or branched $C_1$ to $C_{30}$ alkyl group, and a substituted or unsubstituted $C_6$ to $C_{30}$ aryl group, for another example, hydrogen, a methyl group, and a phenyl group.

The HOMO energy, reorganization energy, and expectation mobility of compounds (1), (3a), (5a), (29a) and (33a) of the compounds (1) to (58) are calculated, and the results are shown in the following Table 1. The HOMO energy and the reorganization energy are calculated by using a Gaussian 09 program in DFT B3LYP/6-31G(d,p) level, and a transfer integral is calculated by using the ADF (Amsterdam Density Functional) program at PW91-TZP, to calculate expectation

TABLE 1

| Compounds | $E_{HOMO}$ (eV) | Reorganization energy (meV) | Expectation mobility $cm^2/Vs$ |
| --- | --- | --- | --- |
| Ref-1 | −5.57 | 146 | 14.3 |
| Ref-2 | −5.52 | 130 | 5.0 |
| Ref-3a | −5.69 | 95 | 20.4 |
| compound 1 | −5.26 | 91 | 23.6 |
| compound 3a | −5.24 | 83 | 37.8 |
| compound 5a | −5.26 | 82 | 26.5 |
| compound 29a | −5.27 | 54 | 26.2 |
| compound 33a | −5.26 | 52 | 49.2 |

As shown in Table 1, the compounds (1), (3a), (5a), (29a) and (33a) have smaller reorganization energy compared with the compounds Ref-1, Ref-2 and Ref-3a, and thus charges may be effectively transported among molecules. The compounds (1), (3a), (5a), (29a) and (33a) show higher expectation mobility compared with the compounds Ref-1, Ref-2, and Ref-3a.

Example embodiments provide an organic thin film including the fused polycyclic heteroaromatic compound and an electronic device including the organic thin film.

The organic thin film according to example embodiments includes the fused polycyclic heteroaromatic compound, so the organic thin film may be applied to an organic semiconductor layer for an electronic device, or a carrier transport layer, e.g., a channel layer. The electronic device including the same may have desirable electrical properties, e.g., relatively high charge mobility, as well as improved processibility and workability.

The organic thin film may be manufactured by depositing the fused polycyclic heteroaromatic compound on a substrate according to the general method, or dissolving the fused polycyclic heteroaromatic compound in an organic solvent and then coating the same at room temperature according to a solution process. If required, a heat treatment may be performed after the deposition or coating process to further enhance the densification and uniformity of the thin film.

Particularly, the organic solvent may include at least one kind of general organic solvent, for example, at least one kind of an aliphatic hydrocarbon solvent, e.g., hexane, heptane, etc.; an aromatic hydrocarbon solvent, e.g., toluene, pyridine, quinoline, anisole, mesitylene, xylene, etc.; a ketone-based solvent, e.g., methyl isobutyl ketone, 1-methyl-2-pyrrolidinone, cyclohexanone, acetone, etc.; an ether-based solvent, e.g., tetrahydrofuran, isopropyl ether, etc.; an acetate-based solvent, e.g., ethyl acetate, butyl acetate, propylene glycol methyl ether acetate, etc.; an alcohol-based solvent, e.g., isopropyl alcohol, butanol, etc.; an amide-based solvent, e.g., dimethyl acetamide, dimethyl formamide, etc.; a silicone-based solvent; and a mixture of solvents. The amount of the fused polycyclic heteroaromatic compound dissolved in the organic solvent may be adequately selected and determined by a person of ordinary skill in the art, for example, in a range of about 0.01 wt % to about 50 wt % of the total solvent in view of solubility and coating property.

The method of providing an organic thin film may include thermal deposition, vacuum deposition, laser deposition, screen printing, printing, imprinting, spin casting, dipping, inkjetting, roll coating, flow coating, drop casting, spray coating, roll printing, etc., but is not limited thereto. The heat treatment may be performed at about 80 to about 250° C. for about 1 minute to about 2 hours, but is not limited thereto.

The thickness of the organic thin film may be adjusted according to the usage and the case considering the kinds of the used compound and solvent by a person of ordinary skill in the art, may be in a range of about 200 Å to about 10,000 Å.

Examples of electronic devices including the organic thin film as a carrier transport layer may include a transistor, an organic light emitting diode (OLED), a photovoltaic device, a solar cell, a laser device, a memory, a sensor, etc., and the organic thin film may be applied to each device according to the general process commonly known in the art.

For example, the transistor includes: a gate electrode disposed on a substrate, a source electrode and a drain electrode facing each other and defining a channel region, an insulation layer electrically insulating the source electrode and drain electrode and the gate electrode, and an active layer including the fused polycyclic heteroaromatic compound formed in the channel region.

The active layer may be obtained by depositing the fused polycyclic heteroaromatic compound, or applying a composition including the fused polycyclic heteroaromatic compound to a solution process, e.g., screen printing, printing, spin coating, dipping, ink jetting, etc. When the active layer is formed by the solution process, the process cost may be reduced, and a relatively wide area device may be effectively manufactured.

Figure 2:
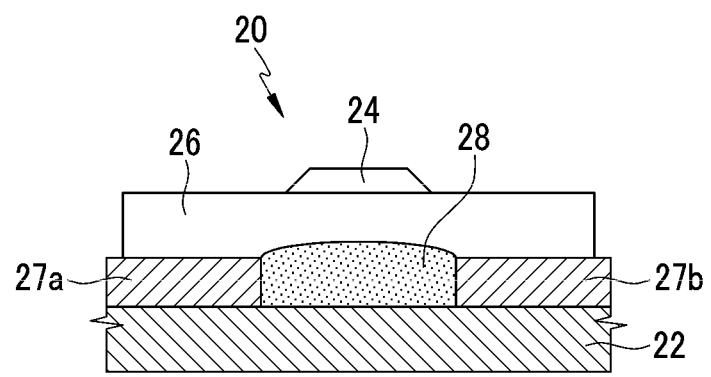
FIG. 2 is a schematic cross-sectional view showing a transistor according to example embodiments.

FIGS. 1 and 2 are schematic cross-sectional views showing a transistor according to example embodiments. The transistor according to example embodiments may be a thin film transistor. The thin film transistor may be a thin film having a thickness of several nanometers to several microns.

Referring to FIG. 1, a transistor 10 includes a substrate 12, a gate electrode 14 disposed on the substrate, and an insulation layer 16 covering the gate electrode 14. A source electrode 17a and a drain electrode 17b defining a channel region are provided on the insulation layer 16, and an active layer 18 is provided in the channel region. The active layer 18 includes the fused polycyclic heteroaromatic compound.

Referring to FIG. 2, a transistor 20 includes a source electrode 27a and a drain electrode 27b defining a channel region and that are formed on a substrate 22, and an active layer 28 formed in the channel region. The active layer 28 includes the fused polycyclic heteroaromatic compound. An insulation layer 26 is formed to cover the source electrode 27a, the drain electrode 27b, and the active layer 28, and a gate electrode 24 is formed thereon.

The substrates 12 and 22 may include an inorganic material, an organic material, or a composite of an inorganic material and an organic material. The organic material may include, for example, a plastic, e.g., polyethylene naphthalate (PEN), polyethylene terephthalate (PET), polycarbonate, polyvinyl alcohol, polyacrylate, polyimide, polynorbornene, and polyethersulfone (PES), and the inorganic material may include, for example, glass or metal.

In addition, the gate electrodes 14 and 24, source electrodes 17a and 27a, and drain electrodes 17b and 27b may include a generally-used metal, particularly, gold (Au), silver (Ag), aluminum (Al), nickel (Ni), or indium tin oxide (ITO), but it is not limited thereto.

The insulation layers 16 and 26 may include a generally-used insulator having a high dielectric constant, particularly, a ferroelectric insulator, e.g., $Ba_{0.33}Sr_{0.66}TiO_3$ (BST, barium strontium titanate), $Al_2O_3$, $Ta_2O_5$, $La_2O_5$, $Y_2O_3$, and $TiO_2$; an inorganic insulator, e.g., $PbZr_{0.33}Ti_{0.66}O_3$ (PZT), $Bi_4Ti_3O_{12}$, $BaMgF_4$, $SrBi_2(TaNb)_2O_9$, $Ba(ZrTi)O_3$ (BZT), $BaTiO_3$, $SrTiO_3$, $SiO_2$, SiNx (x is determined depending on the valence of Si), AlON (aluminum oxynitride), etc.; or an organic insulator, e.g., polyimide, benzocyclobutane (BCB), parylene, polyacrylate, polyvinyl alcohol, polyvinylphenol, etc., but it is not limited thereto. Although it is not mentioned above, the inorganic insulator disclosed in U.S. Pat. No. 5,946,551 and the organic insulator disclosed in U.S. Pat. No. 6,232,157 may be used for the insulation layers 16 and 26.

Hereinafter, the embodiments are illustrated in more detail with reference to examples. However, these are examples, and the present disclosure is not limited thereto.

SYNTHESIS EXAMPLE 1

Synthesis of Fused Polycyclic Heteroaromatic Compound (Compound (1a))

[Reaction Scheme 1]

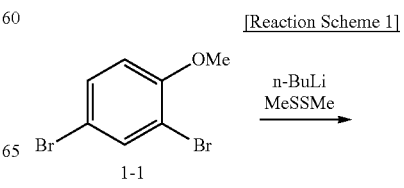

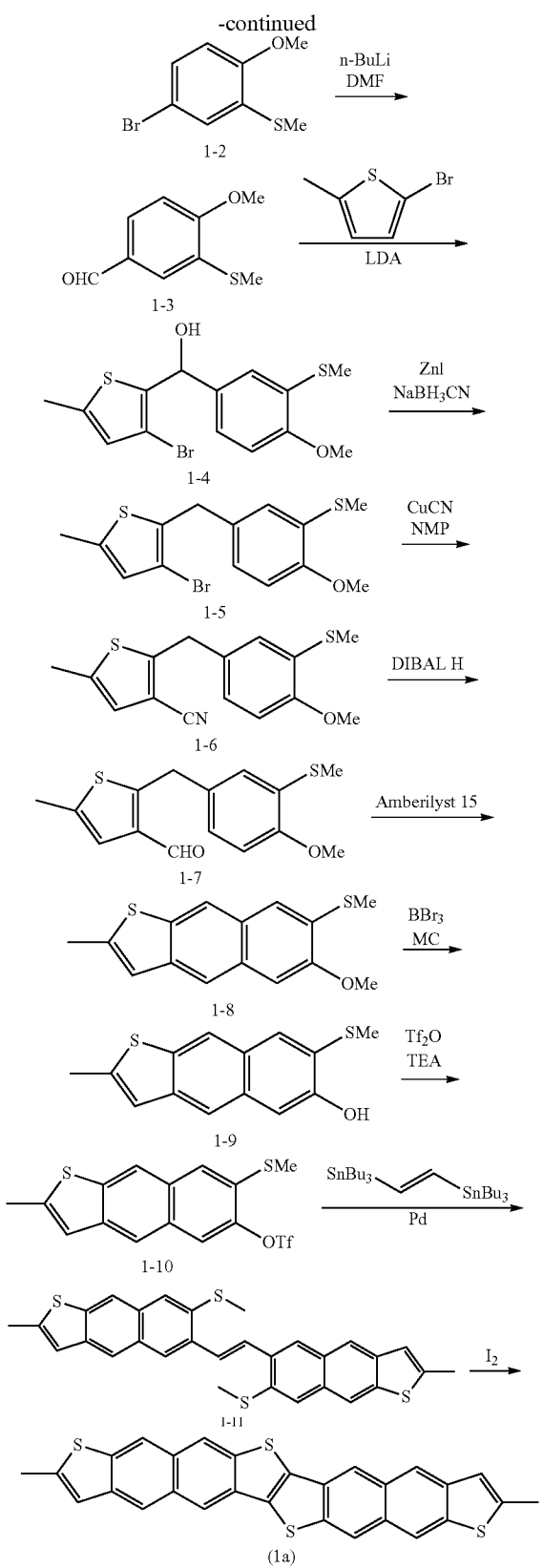

(1) Synthesis of (5-bromo-2-methoxyphenyl)methylsulfane 2,4-dibromo-1-methoxybenzene (20 g, 75 mmol, a compound 1-1) is dissolved in dry diethyl ether (100 mL) under a nitrogen atmosphere, and 2.5 M n-BuLi (in hexane) (332 mL, 0.83 mol) is slowly added thereto in a dropwise fashion at −78° C. The mixture is stirred at the same temperature for 1 hour, and dimethyl disulfide (8.7 mL, 98 mmol) is slowly added thereto. After 30 minutes, an ammonium chloride saturated aqueous solution is added thereto to complete the reaction, and then diethyl ether is used to perform extraction. Then, an organic solvent layer obtained therefrom is dried with anhydrous MgSO$_4$, concentrated, and purified through silica gel column chromatography, obtaining a desired compound 1-2 (yield: 94%).

$^1$H NMR (300 MHz, CDCl$_3$) δ ppm 7.20-7.18 (m, 2H), 6.68 (d, J=8.4 Hz, 1H), 3.86 (s, 3H), 2.42 (s, 3H)

(2) Synthesis of 4-methoxy-3-(methylthio)benzaldehyde

The compound 1-2 (17.3 g, 74 mmol) is dissolved in dry diethyl ether (100 mL), and 2.5 M n-BuLi (in hexane) (32.6 mL, 81 mmol) is slowly added thereto in a dropwise fashion at −78° C. After 1 hour, DMF (dimethyl formamide, 8.6 mL, 110 mmol) is slowly added thereto, and the mixture is stirred at the same temperature for one hour. Subsequently, an ammonium chloride saturated aqueous solution is added thereto to complete the reaction, and then diethyl ether is used to perform extraction. Then, an organic solvent layer obtained therefrom is dried with anhydrous MgSO$_4$, concentrated, and purified through silica gel column chromatography (ethyl acetate (EA):hexane=1:10 volume ratio), obtaining a desired compound 1-3 (yield: 79%).

$^1$H NMR (300 MHz, CDCl$_3$) δ9.87 (s, 1H), 7.67-7.63 (m, 2H), 6.93 (d, J=8.0 Hz, 1H), 3.98 (s, 3H), 2.49 (s, 3H).

(3) Synthesis of (3-bromo-5-methylthiophen-2-yl)(4-methoxy-3-(methylthio)phenyl)methanol Diisopropylamine (4.8 mL, 34 mmol) is dissolved in dry THF (30 mL), 2.5M n-BuLi in hexane (12.6 mL, 32 mmol) is slowly added thereto in a dropwise fashion at −78° C., and the mixture is stirred for 30 minutes. Subsequently, 2-bromo-5-methylthiophene (3 mL, 26.3 mmol) is slowly added thereto at the same temperature, and the mixture is stirred for one hour while slowly increasing its reaction temperature up to −10° C. The reactant is cooled down to −78° C., a compound 1-3 (6.2 g, 34.2 mmol) is added thereto, and the mixture is stirred for 1 hour. Then, an ammonium chloride saturated solution is added thereto to complete the reaction, diethyl ether is used to perform extraction, and an organic solvent layer obtained therefrom is dried with anhydrous MgSO$_4$ and concentrated. The concentrated product is purified through silica gel column chromatography (EA:hexane=1:8 volume ratio), obtaining 9 g of a desired compound 1-4 (yield: 95%).

$^1$H NMR (300 MHz, CDCl$_3$) δ7.29 (s, 1H), 7.20 (d, J=8.4 Hz, 1H), 6.80 (d, J=8.4 Hz, 1H), 6.60 (s, 1H), 6.06 (d, J=3.2 Hz, 1H), 3.88 (s, 3H), 2.43 (s, 3H), 2.40 (s, 3H).

(4) Synthesis of 3-bromo-2-(4-methoxy-3-(methylthio)benzyl)-5-methylthiophene

The compound 1-4 (9 g, 25 mmol) is dissolved in methylene chloride (500 mL), ZnI$_2$ (12 g, 37.5 mmol) is added thereto, after 10 minutes, NaBH$_3$CN (3.15 g, 50.1 mmol) is slowly added thereto, and the mixture is stirred at room temperature (25° C.) for one day. When the reaction is complete, the resultant is filtered with Celite® and then concentrated. The concentrated product is purified through silica gel column chromatography (hexane), obtaining 7.6 g of a desired compound 1-5 (yield: 88%).

$^1$H NMR (300 MHz, CDCl$_3$) δ7.05 (s, 1H), 6.99 (d, J=8.4 Hz, 1H), 6.76 (d, J=8.4 Hz, 1H), 6.58 (s, 1H), 3.97 (s, 2H), 3.87 (s, 3H), 2.41 (s, 3H), 2.38 (s, 3H)

(5) Synthesis of 2-(4-methoxy-3-(methylthio)benzyl)-5-methylthiophene-3-carbonitrile The compound 1-5 (8.5 g, 22 mmol) and CuCN (22 g, 220 mmol) are dissolved in NMP (25 mL), and the solution is heated and stirred at 120° C. for one day. Subsequently, methylene chloride (100 mL) is added thereto, and the mixture is filtered with Celite® to remove an inorganic material therefrom, and an organic layer obtained therefrom is washed with water. The organic solvent layer is dried with anhydrous MgSO$_4$ and then concentrated. The concentrated product is purified through silica gel column chromatography (EA:hexane=1:10 volume ratio), obtaining 5.1 g of a desired compound 1-6 (a yield: 71%).

$^1$H NMR (300 MHz, CDCl$_3$) δ7.05~7.00 (m, 2H), 6.78~6.75 (m, 2H), 4.17 (s, 2H), 3.87 (s, 3H), 2.42 (s, 3H), 2.38 (s, 3H)

(6) Synthesis of 2-(4-methoxy-3-(methylthio)benzyl)-5-methylthiophene-3-carbaldehyde The compound 1-6 (5.1 g, 17.6 mmol) is dissolved in methylene chloride (40 mL), 1 M DIBAL (diisobutylaluminum, in toluene) (19.4 mL, 19.4 mmol) is slowly added thereto in an ice bath, and the mixture is stirred for 3 hours. The reaction is completed when methanol and water each in a small amount is added thereto at the same temperature. Then, an organic solvent layer obtained therefrom is dried with anhydrous MgSO$_4$ and then filtered and concentrated. The concentrated product is purified through silica gel column chromatography (EA:hexane=1:8 volume ratio), obtaining 4 g of a compound 1-7 (yield: 78%).

$^1$H NMR (300 MHz, CDCl$_3$) δ9.99 (s, 1H), 7.04~6.99 (m, 3H), 6.76 (d, J=8.0Hz, 1H), 4.39 (s, 2H), 3.87 (s, 3H), 2.40 (s, 3H), 2.39 (s, 3H)

(7) Synthesis of 6-methoxy-2-methyl-7-(methylthio)naphtho[2,3-b]thiophene

The compound 1-7 (4 g, 13.7 mmol) is dissolved in toluene (40 mL), Amberlyst® 15 (4 g) is added thereto, and the mixture is Dean-Stark heated and reflux-stirred. After 2 hours, the resultant is filtered with Celite® and then concentrated. Then, diethyl ether (80 mL) is added to the concentrated compound to perform precipitation, and the obtained precipitate is filtered, obtaining 3 g of a compound 1-8 (yield: 80%).

$^1$H NMR (300 MHz, CDCl$_3$) δ8.06 (s, 1H), 7.96 (s, 1H), 7.46 (s, 1H), 7.12 (s, 1H), 6.99 (s, 1H), 4.01 (s, 3H), 2.60 (s, 3H), 2.55 (s, 3H)

(8) Synthesis of 2-methyl-7-(methylthio)naphtho[2,3-b]thiophen-6-ol

The compound 1-8 (3 g, 11 mmol) is dissolved in methylene chloride (30 mL), BBr$_3$ (1.6 mL, 16.4 mmol) is slowly added thereto in an ice bath, and the mixture is stirred at room temperature (25° C.) for 2 hours. Subsequently, ice water is added to the reaction mixture to complete the reaction, the resultant is diluted with methylene chloride and washed away with water, and an organic solvent layer obtained therefrom is dried with anhydrous MgSO$_4$ and concentrated. Then, diethyl ether (100 mL) is added to the concentrated compound to perform precipitation, and a precipitate obtained therefrom is filtered, obtaining 2.3 g of a desired compound 1-9 (yield: 81%).

$^1$H NMR (300MHz, CDCl$_3$) δ8.08 (s, 1H), 8.03 (s, 1H), 7.94 (s, 1H), 7.37 (s, 1H), 6.98 (s, 1H), 6.56 (s, 1H), 2.60 (s, 3H), 2.43 (s, 3H)

(9) Synthesis of 2-methyl-7-(methylthio)naphtho[2,3-b]thiophen-6-yl trifluoromethane sulfonate The compound 1-9 (1.04 g, 4 mmol) is dissolved in methylene chloride (40 ml), the solution is cooled down to 0° C., and triethylamine (1.6 ml, 12 mmol) and trifluoromethanesulfonic anhydride (1 ml, 5.5 mmol) are sequentially added thereto in a dropwise fashion. The mixture is stirred at room temperature (25° C.) for 40 hours, a 1N HCl aqueous solution is poured therein to complete the reaction, and methylene chloride is used to perform precipitation. Then, an organic solvent layer obtained therefrom is dried with anhydrous MgSO$_4$ and concentrated. The concentrated product is vacuum-dried, obtaining 1.5 g of a desired compound 1-10 (yield: 95%).

$^1$H NMR (300 MHz, CDCl$_3$) δ8.18 (s, 1H), 8.08(s, 1H), 7.81(s, 1H), 7.71(s, 1H), 7.05(s, 1H), 2.64(s, 3H), 2.61(s, 3H)

(10) Synthesis of Trans-1,2-bis(2-methyl-7-(methylthio)naphtho[2,3-b]thiophen-6-yl) ethene The compound 1-10 (1.18 g, 3 mmol) and trans-1,2-bis(tributylstannyl)ethene (0.91 g, 1.5 mmol) are dissolved in THF (20 ml), and Pd(PPh$_3$)$_4$ (0.18 g, 0.15 mmol) is added thereto. The mixture is heated and refluxed for 20 hours with a reaction flask wrapped with aluminum foil, and then diluted with water. Then, a precipitate produced therein is filtered and washed with water and ethanol, obtaining 0.77 g of a desired compound 1-11 as a yellow solid (yield: 50%).

$^1$H NMR (300 MHz, CDCl$_3$) δ8.19(s, 2H), 8.13(s, 4H), 7.70(s, 2H), 7.67(s, 2H), 7.05(s, 2H), 2.62(s, 6H), 2.61(s, 6H)

(11) Synthesis of di(2-methylthio[7,6-b:7',6'-f]naphthothieno[3,2-b]thiophene

The compound 1-11 (0.62 g, 1.2 mmol) is added to acetic acid (2 ml), iodine powder (7 g, 28 mmol) is added thereto, and the mixture is heated and refluxed for 12 hours. The acetic acid is removed by distillation, a NaHSO$_3$ saturated solution is added thereto, and the mixture is stirred for one hour to remove an excess amount of iodine. Then, a precipitate obtained therefrom is filtered, washed several times with water and acetone, and vacuum-dried, obtaining 0.29 g of a desired compound 1a as a brown solid (yield: 50%).

Maldi-MS m/z=481 (M+1).

SYNTHESIS EXAMPLE 2

Synthesis of Fused Polycyclic Heteroaromatic Compound (Compound (1))

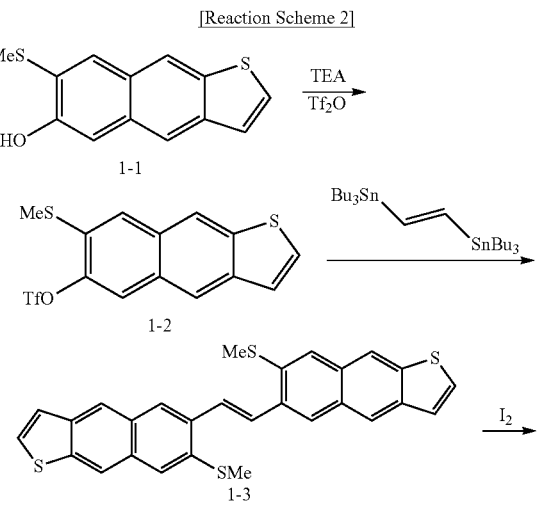

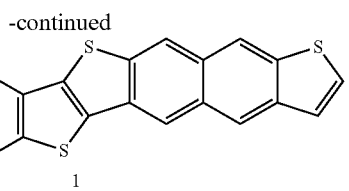

1

(1) Synthesis of 7-(methylthio)naphtho[2,3-b]thiophen-6-yl trifluoromethane sulfonate The compound 1-1 (7 g, 28.41 mmol) is dissolved in methylene chloride (500 ml), the solution is cooled down to 0° C., and then, triethylamine (10.69 ml, 76.72 mmol) and trifluoromethanesulfonic anhydride (6.2 ml, 36.94 mmol) are sequentially added thereto in a dropwise fashion. The mixture is stirred at room temperature (25° C.) for 40 hours, and when the reaction is complete, a 1N HCl aqueous solution is poured thereinto, and methylene chloride is used to perform an extraction. Then, an organic solvent layer obtained therefrom is dried with anhydrous $MgSO_4$ and concentrated. The concentrated product is vacuum-dried, obtaining 8.37 g of a desired compound 1-2 (yield: 78%).

$^1$H NMR (300 MHz, $CDCl_3$) δ8.32 (s, 1H), 8.28 (s, 1H), 7.85 (s, 1H), 7.72 (s, 1H), 7.56 (d, 1H), 7.43 (d, 1H), 2.62 (s, 3H)

(2) Synthesis of Trans-1,2-bis(7-(methylthio)naphtho[2,3-b]thiophen-6-yl) ethene The compound 1-2 (8.37 g, 22.12 mmol) and trans-1,2-bis(tributylstannyl)ethene (5.92 g, 11.06 mmol) are dissolved in THF (100 ml), and $Pd(PPh_3)_4$ (3.83 g, 3.32 mmol) is added thereto. After wrapping the reaction flask with an aluminum foil, the mixture is heated and refluxed for 20 hours and diluted with water. Then, a precipitate obtained therefrom is filtered and washed with water and ethanol, obtaining 2.7 g of a desired compound 1-3 as a yellow solid (yield: 50%).

Maldi-MS m/z=484.72 (M+1).

(3) Synthesis of Di(thio[7,6-b:7',6'-f]naphthothieno[3,2-b]thiophene

The compound 1-3 (2.74 g, 5.65 mmol) is put in chloroform (350 ml), iodine powder (59.5 g, 234.5 mmol) is added thereto, and the mixture is heated and refluxed for 48 hours. The chloroform is removed by distillation, a $NaHSO_3$ saturated solution is added thereto, and the mixture is stirred for 1 hour to remove the excessive amount of the iodine. Then, a precipitate obtained therefrom is filtered, several times washed with water and acetone, and vacuum-dried, obtaining 1.28 g of a desired compound 1 as a brown solid (yield: 50%).

Maldi-MS m/z=452.03 M+1.

SYNTHESIS EXAMPLE 3

Synthesis of Fused Polycyclic Heteroaromatic Compound (Compound (1c))

[Reaction Scheme 3]

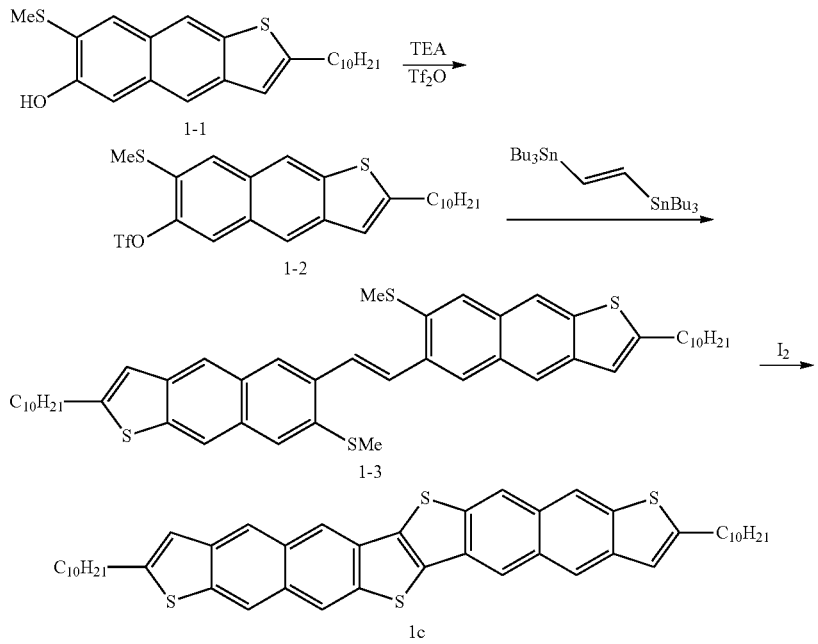

(1) Synthesis of 2-decyl-7-(methylthio)naphtho[2,3-b]thiophene-6-yl trifluoromethane sulfonate The compound 1-1 (7 g, 18.10 mmol) is dissolved in methylene chloride (500 ml), the solution is cooled down to 0° C., and triethylamine (6.81 ml, 48.89 mmol) and trifluoromethanesulfonic anhydride (3.95 ml, 23.54 mmol) are sequentially added thereto in a dropwise fashion. The mixture is stirred at room temperature (25° C.) for 40 hours, and when the reaction is complete, a 1N HCl aqueous solution is poured thereinto, and methylene chloride is used to perform an extraction. Then, an organic solvent layer obtained therefrom is dried with anhydrous $MgSO_4$ and concentrated. The concentrated product is vacuum-dried, obtaining 8.95 g of a desired compound 1-2 (yield: 95%).

$^1$H NMR (300 MHz, $CDCl_3$) δ8.18 (s, 1H), 8.08 (s, 1H), 7.80 (s, 1H), 7.71 (s, 1H), 7.06 (s, 1H), 2.93 (t, 2H), 2.61 (s, 3H), 1.78 (m, 2H), 1.28 (m, 14H), 0.88 (t, 3H)

(2) Synthesis of Trans-1,2-bis(2-decyl-7-(methylthio)naphtho[2,3-b]thiophen-6-yl) ethene The compound 1-2 (8.95 g, 17.26 mmol) and trans-1,2-bis(tributylstannyl)ethene (5.23 g, 8.63 mmol) are dissolved in THF (100 ml), and Pd(PPh$_3$)$_4$ (2.99 g, 2.59 mmol) is added thereto. After wrapping the reaction flask with an aluminum foil, the mixture is heated and refluxed for 20 hours and diluted with water. Then, a precipitate produced therein is filtered and washed with water and ethanol, obtaining 2.36 g of a desired compound 1-3 as a yellow solid (yield: 36%).

$^1$H NMR (300 MHz, CDCl$_3$) δ8.19 (s, 1H), 8.14 (s, 2H), 7.70 (s, 1H), 7.67 (s, 1H), 7.06 (s, 1H), 2.91 (t, 2H), 2.62 (s, 3H), 1.78 (m, 2H), 1.36 (m, 14H), 0.88 (t, 3H)

(3) Synthesis of Di(2-decylthio[7,6-b:7',6'-f]naphthothieno[3,2-b]thiophene

The compound 1-3 (2.36 g, 3.08 mmol) is put in chloroform (300 ml), iodine powder (32.48 g, 128 mmol) is added thereto, and the mixture is heated and refluxed for 48 hours. The chloroform is removed therefrom through distillation, a NaHSO$_3$ saturated solution is added thereto, and the mixture is stirred for 1 hour to remove the excessive amount of the iodine. Then, a precipitate produced therein is filtered, several times washed with water and acetone, and vacuum-dried, obtaining 1.1 g of a desired compound 1c as a brown solid (yield: 50%).

Maldi-MS m/z=733.1 M+1.

SYNTHESIS EXAMPLE 4

Synthesis of Fused Polycyclic Heteroaromatic Compound (Compound (8))

perform an extraction. Then, an organic solvent layer obtained therefrom is dried with anhydrous MgSO$_4$ and concentrated. The concentrated product is vacuum-dried, obtaining 1.21 g of a compound 8-2 (yield: 95%).

$^1$H NMR (300 MHz, CDCl$_3$) δ8.57 (s, 2H), 8.54 (s, 1H), 8.47 (s, 1H), 7.91 (s, 1H), 7.79 (s, 1H), 7.54 (d, 1H), 7.43 (d, 1H), 2.65 (s, 3H)

(2) Synthesis of Trans-1,2-bis(8-(methylthio)antra[2,3-b]thiophen-7-yl) ethene

The compound 8-2 (1.1 g, 2.33 mmol) and trans-1,2-bis(tributylstannyl)ethene (0.63 g, 1.17 mmol) are dissolved in THF (20 ml), and Pd(PPh$_3$)$_4$ (0.4 g, 0.35 mmol) is added thereto. After wrapping the reaction flask with an aluminum foil, the mixture is heated and refluxed for 20 hours and diluted with water. Then, a precipitate produced therein is filtered and washed with water and ethanol, obtaining 0.26 g of a compound 8-3 as a yellow solid (yield: 43%).

Maldi-MS m/z=584.8 M+1.

(3) Synthesis of Compound 8

The compound 8-3 (0.25 g, 0.45 mmol) is put in chloroform (50 ml), iodine powder (4.56 g, 18.99 mmol) is added thereto, and the mixture is heated and refluxed for 48 hours. The chloroform is removed therefrom through distillation, a NaHSO$_3$ saturated solution is added thereto, and the mixture is stirred for 1 hour to remove the excessive amount of the iodine. Then, a precipitate produced therein is filtered, several times washed with water and acetone, and vacuum-dried, obtaining 0.12 g of a desired compound 8 as a reddish brown solid (yield: 50%).

Maldi-MS m/z=552.7 M+1.

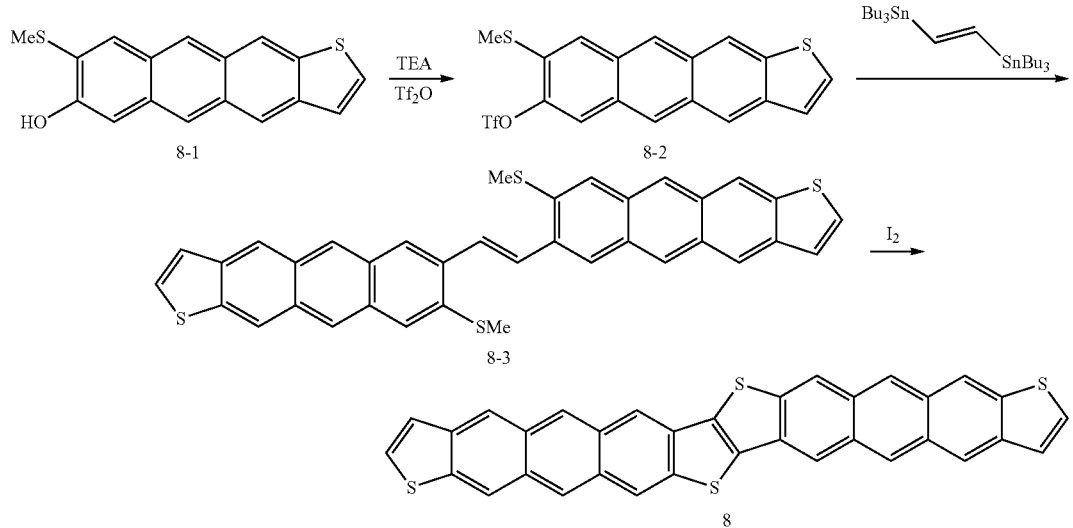

[Reaction Scheme 4]

(1) Synthesis of 8-(methylthio)anthra[2,3-b]thiophen-7-yl trifluoromethene sulfonate The compound 8-1 (1.0 g, 3.37 mmol) is dissolved in methylene chloride (100 ml), the solution is cooled down to 0° C., and triethylamine (1.27 ml, 9.1 mmol) and trifluoromethanesulfonic anhydride (0.74 ml, 4.39 mmol) are sequentially added thereto in a dropwise fashion. The mixture is stirred at room temperature (25° C.) for 40 hours, and when the reaction is complete, a 1N HCl aqueous solution is poured thereinto, and methylene chloride is used to Thermal Stability of Fused Polycyclic Heteroaromatic Compound Thermal stability of the compounds according to Synthesis Examples 1 to 4 was evaluated by measuring their thermal degradation temperatures. The thermal degradation temperature (T$_d$) is a temperature that the compounds start to be decomposed and thus do not maintain their intrinsic molecules structure but are transformed. In general, since an atom in a molecule of a compound is volatilized and lost into an atmosphere or vacuum, the thermal degradation temperature may be evaluated as a temperature that the initial weight of the compound starts to be reduced by heat. Herein, the thermal degradation temperature is measured in a thermal gravimetric analysis (TGA) method. Superficially, 1 wt % of the compound according to Synthesis Example 2 is lost at 468° C., and 1 wt % of the compound of Ref-1 is lost at 339° C. Accordingly, the compound according to Synthesis Example 2 shows improved thermal stability.

EXAMPLES 1 TO 4

Manufacture of Organic Thin Film Transistor Using Fused Polycyclic Heteroaromatic Compound First, a silicon substrate covered with a 3000 Å silicon oxide film is rinsed with isopropyl alcohol for 10 minutes. The rinsed silicon substrate is treated with oxygen plasma, dipped in an octadecyl trichlorosilane solution that is diluted to a 5 mM concentration in hexane, for 30 minutes, is rinsed with hexane and ethanol, then baked at 120° C. for 30 minutes, and then is washed with ultrasonic waves in a chloroform solvent. The washed silicon substrate is dried, and each fused polycyclic heteroaromatic compound according to Synthesis Examples 1 to 4 is applied at a thickness of 700 A using vacuum thermal deposition. Au as a source-drain electrode is sputtered at a thickness of 1000 A thereon to manufacture an organic thin film transistor (OTFT) device.

COMPARATIVE EXAMPLES 1 to 4

Manufacture of Organic Thin Film Transistor Using Fused Polycyclic Heteroaromatic Compound An organic thin film transistor (OTFT) is manufactured according to the same method as Examples 1 to 4 except for using a compound provided in Table 2 instead of the fused polycyclic heteroaromatic compounds according to Synthesis Examples 1 to 4.

Charge mobility of the organic thin film transistors according to Examples 1 to 4 and Comparative Examples 1 to 4 is calculated.

The charge mobility of the organic thin film transistor is obtained by drawing a graph with $(I_{SD})^{1/2}$ and $V_G$ as a variable from a saturation region equation and then, calculating a slope from the graph:

$$I_{SD} = \frac{WC_0}{2L}\mu(V_G - V_T)^2 \qquad \text{[Equation 1]}$$

$$\sqrt{I_{SD}} = \sqrt{\frac{\mu C_0 W}{2L}}(V_G - V_T)$$

$$\text{slope} = \sqrt{\frac{\mu C_0 W}{2L}}$$

$$\mu_{FET} = (\text{slope})^2 \frac{2L}{C_0 W}$$

In Equation 1, $I_{SD}$ refers to a source-drain current, $\mu$ or $\mu_{FET}$ refers to charge mobility, $C_O$ refers to oxide layer capacitance, W is a channel width, L is a channel length, $V_G$ is a gate voltage, and $V_T$ is a threshold voltage.

Herein, charge mobility results of Example 2 and Comparative Example 1 to 4 are provided in Table 2.

TABLE 2

| | Chemical Formula | Mobility (cm²/Vs) |
|---|---|---|
| Comparative Example 1 | 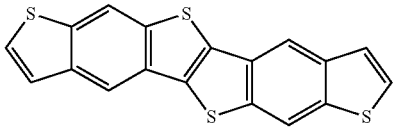 [SMILES: c1cc2cc3c(cc2s1)sc1c2cc4ccsc4cc2sc31] | 10 |
| Comparative Example 2 | 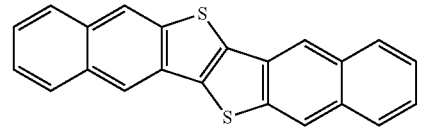 [SMILES: c1ccc2cc3c(cc2c1)sc1c2cc4ccccc4cc2sc31] | 3.1 |
| Comparative Example 3 | 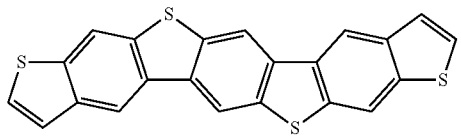 [SMILES: c1cc2cc3c(cc2s1)sc1cc2c(cc13)sc1cc3sccc3cc12] | 2 |
| Comparative Example 4 | 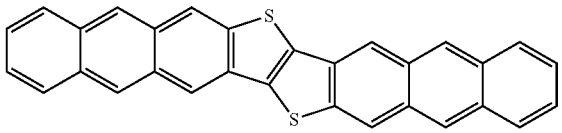 [SMILES: c1ccc2cc3cc4c(cc3cc2c1)sc1c2cc3cc5ccccc5cc3cc2sc41] | 3.0 |

TABLE 2-continued

| | Chemical Formula | Mobility (cm²/Vs) |
|---|---|---|
| Example 2 | (structure) | 13 |

Referring to Table 2, the organic thin film transistor of Example 2 including the compound of Synthesis Example 2 including 8 aromatic rings shows improved mobility compared with the organic thin film transistor of Comparative Example 1 or 2 including a compound (Ref-1, Ref-2) including 6 aromatic rings and the organic thin film transistor of Comparative Example 3 including a compound including 7 aromatic rings. In addition, the organic thin film transistor of Example 2 including the compound of Synthesis Example 2 having a thiophene ring shows improved mobility compared with the organic thin film transistor of Comparative Example 4 including a compound having a phenylene ring as the outermost ring.

While this disclosure has been described in connection with what is presently considered to be practical example embodiments, it is to be understood that the inventive concepts are not limited to the disclosed embodiments, but, on the contrary, is intended to cover various modifications and equivalent arrangements included within the spirit and scope of the appended claims.

What is claimed is:

1. A fused polycyclic heteroaromatic compound represented by Chemical Formula 1A

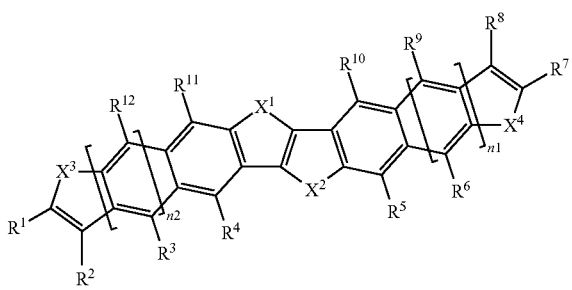

wherein, in Chemical Formula 1A,
each of $X^1$ to $X^4$ are independently O, S, Se, Te, N—$R^a$, or —NC(=O)O$R^f$,
wherein each $R^a$ is independently hydrogen, a substituted or unsubstituted linear or branched $C_1$ to $C_{30}$ alkyl group, a substituted or unsubstituted $C_2$ to $C_{30}$ alkenyl group, a substituted or unsubstituted $C_2$ to $C_{30}$ alkynyl group, a substituted or unsubstituted $C_7$ to $C_{30}$ arylalkyl group, a substituted or unsubstituted $C_6$ to $C_{30}$ aryl group, or a substituted or unsubstituted $C_1$ to $C_{30}$ alkoxy group, and
wherein $R^f$ is a substituted or unsubstituted $C_1$ to $C_{30}$ alkyl group,
each of $R^1$ to $R^{12}$ are independently hydrogen, a substituted or unsubstituted $C_1$ to $C_{30}$ alkyl group, a substituted or unsubstituted $C_1$ to $C_{30}$ alkoxy group, a substituted or unsubstituted $C_2$ to $C_{30}$ alkenyl group, a substituted or unsubstituted $C_2$ to $C_{30}$ alkynyl group, a substituted or unsubstituted $C_6$ to $C_{30}$ aryl group, a substituted or unsubstituted $C_2$ to $C_{30}$ heteroaryl group, a substituted or unsubstituted $C_7$ to $C_{30}$ arylalkyl group, a substituted or unsubstituted $C_2$ to $C_{30}$ heteroarylalkyl group, a substituted or unsubstituted $C_2$ to $C_{30}$ alkylheteroaryl group, a substituted or unsubstituted $C_5$ to $C_{30}$ cycloalkyl group, or a substituted or unsubstituted $C_2$ to $C_{30}$ heterocycloalkyl group,
each of n1 and n2 are independently 1, 2, or 3.

2. The fused polycyclic heteroaromatic compound of claim 1, wherein each of the $R^1$ and $R^7$ groups are independently a substituted or unsubstituted $C_1$ to $C_{30}$ alkyl group, a substituted or unsubstituted $C_6$ to $C_{30}$ aryl group, a substituted or unsubstituted $C_2$ to $C_{30}$ heteroaryl group, a substituted or unsubstituted $C_7$ to $C_{30}$ arylalkyl group, a substituted or unsubstituted $C_2$ to $C_{30}$ heteroarylalkyl group, a substituted or unsubstituted $C_2$ to $C_{30}$ alkylheteroaryl group, a substituted or unsubstituted $C_5$ to $C_{30}$ cycloalkyl group, or a substituted or unsubstituted $C_2$ to $C_{30}$ heterocycloalkyl group.

3. The fused polycyclic heteroaromatic compound of claim 1, wherein each of the $R^1$ and $R^7$ groups are independently a fluoro-substituted $C_1$ to $C_{30}$ alkyl group.

4. The fused polycyclic heteroaromatic compound of claim 1, wherein Ra is a substituted or unsubstituted $C_{10}$ to $C_{30}$ alkyl group, or a substituted or unsubstituted $C_{10}$ to $C_{30}$ alkoxy group, a substituted or unsubstituted $C_{10}$ to $C_{30}$ alkenyl group, or a substituted or unsubstituted $C_{10}$ to $C_{30}$ alkynyl group.

5. The fused polycyclic heteroaromatic compound of claim 1, wherein the $R^a$ is a fluoro-substituted $C_1$ to $C_{30}$ alkyl group.

6. The fused polycyclic heteroaromatic compound of claim 1, wherein the fused polycyclic heteroaromatic compound has an average molecular weight of about 350 to about 3,000.

7. The fused polycyclic heteroaromatic compound of claim 1, wherein n1 and n2 are each 1.

8. The fused polycyclic heteroaromatic compound of claim 1, wherein n1 and n2 are independently 2 or 3.

9. The fused polycyclic heteroaromatic compound of claim 1, wherein $X^1$ and $X^2$ are S.

10. The fused polycyclic heteroaromatic compound of claim 1, wherein $X^1$ and $X^2$ are O.

11. The fused polycyclic heteroaromatic compound of claim 1, wherein $X^1$ and $X^2$ are Te.

12. The fused polycyclic heteroaromatic compound of claim 1, wherein each of $X^1$ to $X^2$ are N—$R^a$.

13. The fused polycyclic heteroaromatic compound of claim 1, wherein n1 and n2 are 1.

14. The fused polycyclic heteroaromatic compound of claim 13, wherein $X^1$ to $X^4$ are S.

15. The fused polycyclic heteroaromatic compound of claim 1, wherein the compound is at least one of compounds (1), (1a), (3), (5), (7), (9), (11), (13), (15), (17), (19), (21), (23), and (25):

(1)
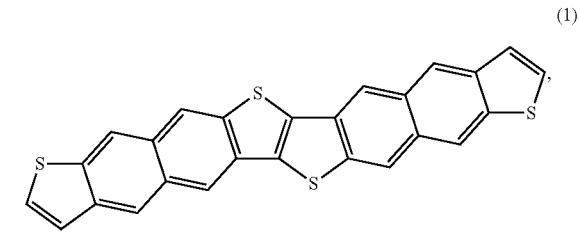
(1a)
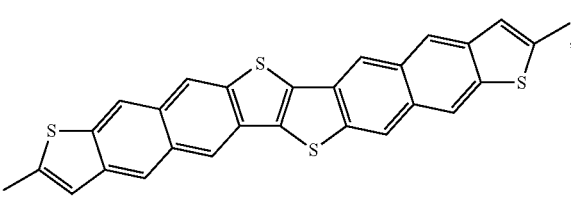
(3)
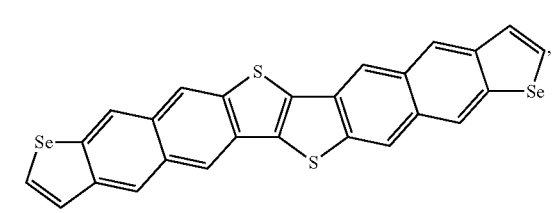
(5)
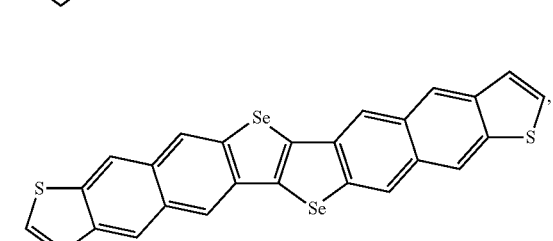
(7)
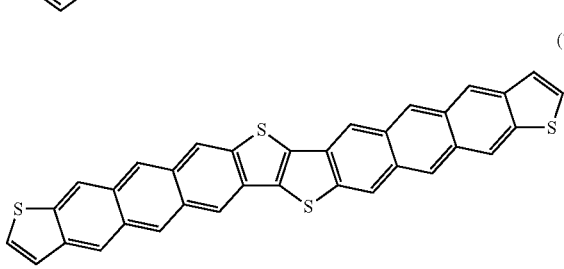
(9)
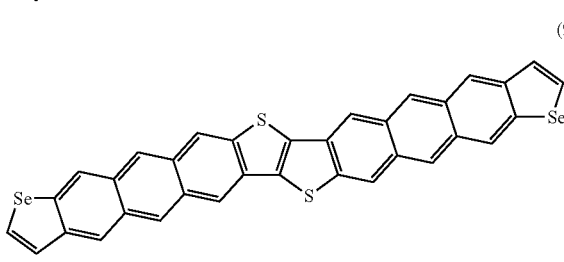
(11)
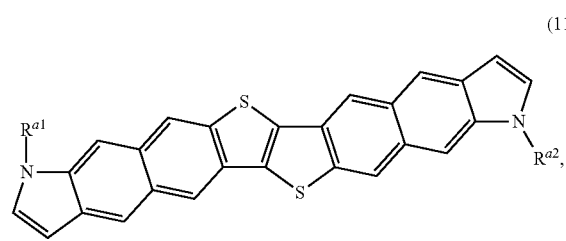
(13)
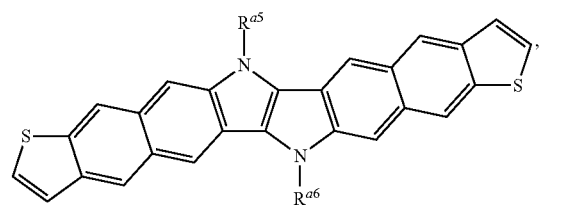
(15)
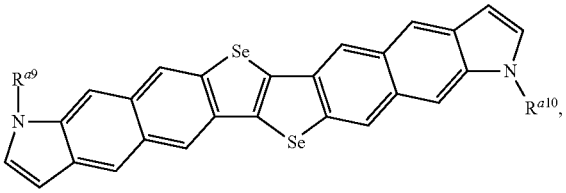
(17)
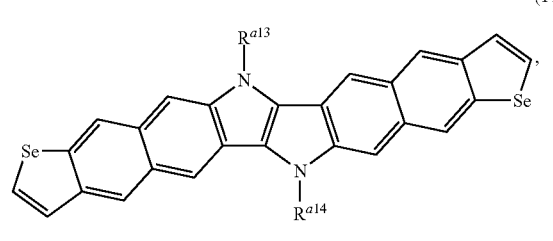
(19)
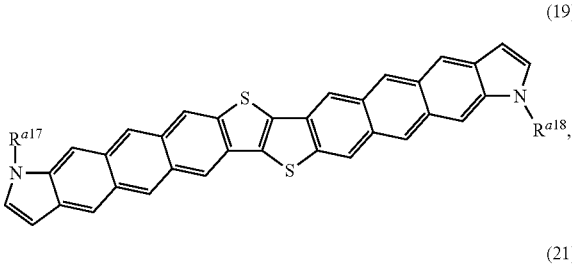
(21)
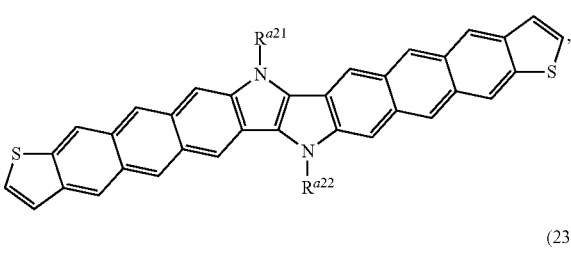
(23)
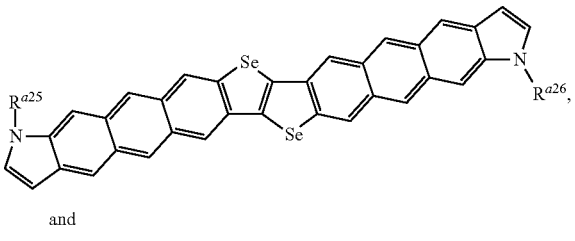
and -continued (25)

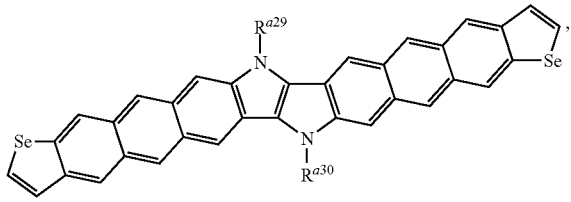

wherein:
a hydrogen of each benzene ring, each thiophene ring, each selenophene ring or each pyrrole ring is optionally replaced by a substituted or unsubstituted $C_1$ to $C_{30}$ alkyl group, a substituted or unsubstituted $C_1$ to $C_{30}$ alkoxy group, a substituted or unsubstituted $C_2$ to $C_{30}$ alkenyl group, a substituted or unsubstituted $C_2$ to $C_{30}$ alkynyl group, a substituted or unsubstituted $C_6$ to $C_{30}$ aryl group, a substituted or unsubstituted $C_2$ to $C_{30}$ heteroaryl group, a substituted or unsubstituted $C_7$ to $C_{30}$ arylalkyl group, a substituted or unsubstituted $C_2$ to $C_{30}$ heteroarylalkyl group, a substituted or unsubstituted $C_2$ to $C_{30}$ alkylheteroaryl group, a substituted or unsubstituted $C_5$ to $C_{30}$ cycloalkyl group, or a substituted or unsubstituted $C_2$ to $C_{30}$ heterocycloalkyl group; and in $R^{a1}$, $R^{a2}$, $R^{a5}$, $R^{a6}$, $R^{a9}$, $R^{a10}$, $R^{a13}$, $R^{a14}$, $R^{a17}$, $R^{a18}$, $R^{a21}$, $R^{a22}$, $R^{a25}$, $Ra^{26}$, $R^{a29}$, and $R^{a30}$ of the compounds (11), (13), (15), (17), (19), (21), (23), and (25) are independently the same as $R^a$ of Chemical Formulae 1A.

16. The fused polycyclic heteroaromatic compound of claim 15, wherein $R^{a1}$, $R^{a2}$, $R^{a5}$, $R^{a6}$, $R^{a9}$, $R^{a10}$, $R^{a13}$, $R^{a14}$, $R^{a17}$, $R^{a18}$, $R^{a21}$, $R^{a22}$, $R^{a25}$, $R^{a26}$, $R^{a29}$, and $R^{a30}$ of the compounds (11), (13), (15), (17), (19), (21), (23), and (25), respectively, are independently hydrogen, a substituted or unsubstituted linear or branched $C_1$ to $C_{30}$ alkyl group, or a substituted or unsubstituted $C_6$ to $C_{30}$ aryl group.

17. An organic thin film comprising the fused polycyclic heteroaromatic compound of claim 1.

18. An electronic device comprising the fused polycyclic heteroaromatic compound of claim 1.

19. The electronic device of claim 18, wherein the electronic device is a transistor, an organic light emitting diode (OLED), a photovoltaic device, a solar cell, a laser device, a memory device, or a sensor.

20. The electronic device of claim 18, wherein
the electronic device includes at least one charge transport layer; and
the charge transport layer includes the fused polycyclic heteroaromatic compound.

* * * * *